US008901913B2

(12) United States Patent
Zhu et al.

(10) Patent No.: US 8,901,913 B2
(45) Date of Patent: Dec. 2, 2014

(54) MICROELECTRODE ARRAYS

(75) Inventors: Jing Zhu, Beijing (CN); Zhongyao Yu, Beijing (CN); Xueling Quan, Beijing (CN); Guangxin Xiang, Beijing (CN); Yuming Hu, Beijing (CN); Wanli Xing, Beijing (CN); Jing Cheng, Beijing (CN)

(73) Assignee: CapitalBio Corporation, Beijing (CN)

( * ) Notice: Subject to any disclaimer, the term of this patent is extended or adjusted under 35 U.S.C. 154(b) by 427 days.

(21) Appl. No.: 12/424,955

(22) Filed: Apr. 16, 2009

(65) Prior Publication Data

US 2009/0322309 A1 Dec. 31, 2009

(30) Foreign Application Priority Data

Jun. 27, 2008 (CN) .......................... 2008 1 0115784

(51) Int. Cl.
*G01N 27/00* (2006.01)
*G01N 33/483* (2006.01)

(52) U.S. Cl.
CPC .................................. *G01N 33/4836* (2013.01)
USPC ................ 324/71.1; 204/403.01; 204/403.13; 435/4; 435/7.1; 435/173.1; 435/287

(58) Field of Classification Search
USPC ........................................................ 324/71.1
See application file for complete search history.

(56) References Cited

U.S. PATENT DOCUMENTS

| 3,513,384 | A | * | 5/1970 | Schneider ...................... 324/450 |
| 4,433,886 | A | * | 2/1984 | Cassarly et al. ................. 439/65 |
| 4,920,047 | A | | 4/1990 | Giaever et al. |
| 5,187,096 | A | | 2/1993 | Giaever et al. |
| 5,204,239 | A | * | 4/1993 | Gitler et al. ..................... 435/7.1 |
| 6,051,422 | A | * | 4/2000 | Kovacs et al. .............. 435/287.1 |
| 6,437,551 | B1 | | 8/2002 | Krulevitch et al. |
| 6,758,961 | B1 | * | 7/2004 | Vogel et al. ................. 205/777.5 |
| RE40,209 | E | * | 4/2008 | Sugihara et al. ........... 435/287.1 |

(Continued)

FOREIGN PATENT DOCUMENTS

| CN | 1996001 A | 7/2007 | |
| TW | 200830963 A | * | 8/2008 | ............. H05K 3/34 |
| WO | 2004/010102 A2 | 1/2004 | |
| WO | 2004/010103 A2 | 1/2004 | |

OTHER PUBLICATIONS

Arndt, S., et al., "Bioelectrical Impedance Assay to Monitor Changes in Cell Shape During Apoptosis," Biosensors and Bioelectronics, 19(6):583-594, Jan. 2004.

(Continued)

*Primary Examiner* — Benjamin M Baldridge
(74) *Attorney, Agent, or Firm* — Perkins Coie LLP

(57) ABSTRACT

Among others things, techniques, systems, and apparatus are disclosed for recording electrophysiological signals. In one aspect, a microelectrode sensing device includes a printed circuit board (PCB), a chip unit electrically connected to the PCB, and a cell culture chamber positioned over the chip unit and sealed to the PCB with the chip unit between the PCB and the cell culture chamber. The chip unit includes a substrate; a conductive layer positioned over the substrate that includes one or more recording electrodes; an insulation layer positioned over the conductive layer; another conductive layer positioned over the insulation layer that includes positioning electrodes; and another insulation layer positioned over the other conductive layer. The recording and positioning electrodes are electrically independent so as to independently receive a stimulus signal at each recording electrode and positioning electrode and independently detect a sensed signal at each recording electrode.

15 Claims, 23 Drawing Sheets

(56) References Cited

U.S. PATENT DOCUMENTS

| | | | |
|---|---|---|---|
| 7,375,404 B2* | 5/2008 | Park et al. | 257/414 |
| 7,381,906 B2* | 6/2008 | Holmberg | 174/385 |
| 7,462,324 B2* | 12/2008 | Ozaki et al. | 422/82.01 |
| 7,534,968 B2* | 5/2009 | English et al. | 174/382 |
| 7,833,396 B2* | 11/2010 | Fukushima | 204/403.01 |
| 2002/0182591 A1 | 12/2002 | Giaever et al. | |
| 2003/0164295 A1* | 9/2003 | Sterling | 204/450 |
| 2004/0128633 A1 | 7/2004 | Weller et al. | |
| 2004/0152067 A1* | 8/2004 | Wang et al. | 435/4 |
| 2004/0163953 A1 | 8/2004 | Bhullar et al. | |
| 2005/0004442 A1* | 1/2005 | Ozaki et al. | 600/407 |
| 2005/0067279 A1* | 3/2005 | Chen et al. | 204/403.13 |
| 2005/0130119 A1 | 6/2005 | Giaever et al. | |
| 2005/0153425 A1* | 7/2005 | Xu et al. | 435/287.1 |
| 2005/0211556 A1* | 9/2005 | Childers et al. | 204/518 |
| 2005/0213374 A1 | 9/2005 | Xu et al. | |
| 2005/0230767 A1* | 10/2005 | Park et al. | 257/414 |
| 2005/0252777 A1 | 11/2005 | Li | |
| 2006/0057771 A1* | 3/2006 | Kovacs et al. | 438/106 |
| 2006/0105321 A1 | 5/2006 | Moy et al. | |
| 2006/0121446 A1 | 6/2006 | Abassi et al. | |
| 2006/0151324 A1 | 7/2006 | Davies et al. | |
| 2006/0188904 A1* | 8/2006 | Ozkan et al. | 435/6 |
| 2007/0054317 A1* | 3/2007 | Diebold et al. | 435/7.1 |
| 2007/0077656 A1* | 4/2007 | Yu | 435/440 |
| 2007/0105089 A1* | 5/2007 | Deutsch | 435/4 |
| 2007/0155015 A1* | 7/2007 | Vassanelli et al. | 435/461 |
| 2007/0172939 A1* | 7/2007 | Xu et al. | 435/287.1 |
| 2007/0190665 A1* | 8/2007 | Kasahara et al. | 436/514 |
| 2007/0228403 A1* | 10/2007 | Choi et al. | 257/98 |
| 2007/0242105 A1* | 10/2007 | Srinivasan et al. | 347/63 |
| 2007/0259577 A1* | 11/2007 | Stromiedel | 439/886 |
| 2007/0275435 A1* | 11/2007 | Kim et al. | 435/29 |
| 2007/0296425 A1* | 12/2007 | LaMeres et al. | 324/754 |
| 2008/0083617 A1 | 4/2008 | Simpson et al. | |
| 2008/0102464 A1* | 5/2008 | Abeygunaratne | 435/6 |
| 2008/0106884 A1* | 5/2008 | English et al. | 361/818 |
| 2008/0176422 A1* | 7/2008 | Philipsson | 439/76.1 |
| 2008/0202806 A1* | 8/2008 | Holmberg | 174/384 |
| 2008/0286750 A1* | 11/2008 | Xu et al. | 435/4 |
| 2009/0057147 A1* | 3/2009 | Kayyem | 204/403.01 |
| 2009/0251155 A1 | 10/2009 | Wang et al. | |
| 2009/0325256 A1* | 12/2009 | Yasukawa et al. | 435/173.1 |
| 2010/0019756 A1* | 1/2010 | Hiraoka et al. | 324/71.1 |
| 2010/0144558 A1* | 6/2010 | Zenhausern et al. | 506/39 |
| 2010/0184115 A1 | 7/2010 | Wang et al. | |
| 2010/0248284 A1* | 9/2010 | Chen et al. | 435/29 |
| 2010/0270176 A1* | 10/2010 | Xiang et al. | 205/777.5 |

OTHER PUBLICATIONS

Bieberich, E., et al., "Neuronal Differentiation and Synapse Formation of PC12 and Embryonic Stem Cells on Interdigitated Microelectrode Arrays: Contact Structures for Neuron-to-Electrode Signal Transmission (NEST)," Biosensors and Bioelectronics, 19(8):923-931, Mar. 2004.

Giaever, I., et al., "Micromotion of Mammalian Cells Measured Electrically," Proceedings of the National Academy of Science of the USA, 88(17):7896-7900, Sep. 1991.

Giaever, I., et al., "Monitoring Fibroblast Behavior in Tissue Culture with an Applied Electric Field," Proceedings of the National Academy of Science of the USA, 81(12):3761-3764, Jun. 1984.

Huang, X., et al., "Simulation of microelectrode impedance changes due to cell growth," IEEE Sensors Journal, 4 (5):576-583, 2004.

Wegener, J., et al., "Electric Cell-Substrate Impedance Sensing (ECIS) as a Noninvasive Means to Monitor the Kinetics of Cell Spreading to Artificial Surfaces," Experimental Cell Research, 259(1):158-166, Aug. 2000.

Xiao, C., et al., "An in-depth analysis of electric cell-substrate impedance sensing to study the attachment and spreading of mammalian cells," Analytical Chemistry, 74(6):1333-1339, Feb. 2002.

Xiao, C., et al., "Online Monitoring of cell growth and cytotoxicity using electric cell-substrate impedance sensing (ECIS)," Biotechnology Progress, 19:1000-1005, 2003.

Xing, J.Z., et al., "Dynamic Monitoring of Cytotoxicity on Microelectronic Sensors," Chemical Research in Toxicology, 18(2):154-161, Feb. 2005.

Yu, N., et al., "Real-time monitoring of morphological changes in living cells by electronic cell sensor arrays : An approach to study G protein-coupled receptors," Analytical Chemistry, 78(1):35-43, Jan. 2006.

International Search Report dated Feb. 28, 2008 for International Application No. PCT/CN2007/002260, filed Jul. 25, 2007 (4 pages).

European Search Report dated Apr. 21, 2010 for European Patent Application No. 08169204.8, filed Oct. 7, 2003 (9 pages).

Yong, Li, et al., "A method for patterning multiple types of cells by using electrochemical desorption of self-assembled monolayers within microfluidic channels," Angewandte Chemie, 46(7):1094-1096, 2007.

Wang, L., et al., "An automatic and quantitative on-chip cell migration assay using self-assembled monolayers combined with real-time cellular impedance sensing," Lab on a Chip, 8(6):872-828, Jun. 2008.

Nie, et al., "On-chip cell migration assay using microfluidic channels," Biomaterials, Elsevier science publishers, 28 (27):4017-4022, Jul. 2007.

Jiang, X., et al., "Electrochemical desorption of self-assembled monolayers noninvasively releases patterned cells from geometrical confinements," Journal of the American Chemical Society, 125(9):2366-2367, Mar. 2003.

Bowen, C.R., et al., "Optimisation of interdigitated electrodes for piezoelectric actuators and active fibre composites," Journal of Electroceram, 16:263-269, 2006.

Giaever, I., et al., "A morphological biosensor for mammalian cells," Nature, 366:591-592, Dec. 1993.

Greve, D.W., et al., "Modeling of impedance of cell-covered electrodes," Sensors Conference, Proceedings of IEEE, 2:1358-1363, 2003.

* cited by examiner

MICROELECTRODE ARRAYS

CLAIM OF PRIORITY

This application claims priority to Chinese Patent Application No. 200810115784.7, filed on Jun. 27, 2008 in the State Intellectual Property Office of the People's Republic of China, the entire contents of which are hereby incorporated by reference.

BACKGROUND

This application related to microelectrode sensing devices.

Microelectrode arrays (MEAs) can be used to facilitate electrophysiological measurements of excitable cells (e.g., neuronal cells). Electrophysiological measurements can be obtained under various conditions. For example, pharmacological studies can be performed by applying various chemical compounds onto the neuronal cells and recording the resultant electrical activities.

Higher amplitude of electrophysiological signals and improved effectiveness of stimulation can be achieved by positioning neurons on or closely in the neighborhood of a recording/stimulation site. Attempts to provide such controlled positioning of neuronal cells by employing physical containment such as micro-wells and micro-channels and/or appropriate materials to obtain desirable cell patterns have been mostly unsatisfactory.

SUMMARY

Techniques, systems and apparatus are described for performing cell manipulation and electrophysiological detection using microelectrode sensing devices.

In one aspect, a microelectrode sensing device includes a printed circuit board (PCB) and a chip unit electrically connected to the PCB. The chip unit includes a substrate; a conductive layer positioned over the substrate that includes one or more recording electrodes; an insulation layer positioned over the conductive layer; another conductive layer positioned over the insulation layer that includes positioning electrodes (e.g., four or more); and another insulation layer positioned over the other conductive layer. The microelectrode sensing device includes a cell culture chamber positioned over the chip unit and sealed to the PCB with the chip unit between the PCB and the cell culture chamber. The recording and positioning electrodes are electrically independent so as to independently apply a stimulus signal at each recording electrode and positioning electrode and independently detect a sensed electrical signal at each recording electrode.

Implementations can optionally include one or more of the following features. The chip unit can be electrically connected to the PCB by wire bonding. The PCB can include two rows of contact pads arranged to surround the chip unit, and the chip unit can include contact pads distributed at each edge of the chip unit. The chip unit can be electrically connected to the PCB using electrical connections between the contact pads of the PCB and the contact pads of the chip unit. The PCB can include additional contact pads located at each edge of the PCB. At least one of the two rows of contact pads of the PCB that surround the chip unit is electrically connected to the additional contact pads located at each edge of the PCB using conductive wires shaped to form an arc. The contact pads of the chip unit can be equally spaced apart at the edge of the chip unit. Each of the recording and positioning electrodes can be separately connected to a separate one of the contact pads on the chip unit. Each of the recording and positioning electrodes can be separately connected to a separate one of the contact pads on the chip unit using a conductive wire shaped to form an arc. A width of the conductive wire can be shaped to increase from the recording electrodes to the contact pads on the chip unit. The two conductive layers can include ground electrodes connected through a passage at the insulation layer that is between the two conductive layers and arranged to separate the wire connecting each of the recording and positioning electrodes to the contact pads on the chip unit. A surface of each recording electrode can include spongy material. The spongy material can include platinum black. The substrate of the chip unit can include glass wafer. Each positioning electrode can be shaped to form a ring. Each insulation layer can include two layers of $Si_3N_4$ and $SiO_2$.

In another aspect, a system includes a microelectrode sensing device that includes a printed circuit board (PCB) and a chip unit electrically connected to the printed circuit board. The chip unit includes a substrate; a conductive layer positioned over the substrate that includes one or more recording electrodes; an insulation layer positioned over the conductive layer; another conductive layer positioned over the insulation layer that includes positioning electrodes; and another insulation layer positioned over the other conductive layer. The microelectrode sensing device includes a cell culture chamber positioned over the chip unit and sealed to the PCB with the chip unit between the PCB and the cell culture chamber. The recording and positioning electrodes are electrically independent so as to independently apply a stimulus signal at each recording electrode and positioning electrode and independently detect a sensed signal at each recording electrode. The system includes a metal clamp connected to the microelectrode sensing device. The metal clamp includes a metal enclosure to receive the microelectrode sensing device; a cover plate detachably connected to the metal enclosure to hold the received microelectrode sensing device against metal enclosure; and another PCB. The other PCB on the metal clamp includes positioning structures to provide a connection to the metal enclosure, and spring-pins to provide an electrical connection to the PCB of the microelectrode sensing device.

Implementations can optionally include one or more of the following features. The metal enclosure can include guidepaths corresponding to a shape of the microelectrode sensing device to restrict movement of the microelectrode sensing device along a direction of movement of the spring-pins. The cover plate can be placed on top of the microelectrode sensing device to press the microelectrode sensing device tightly against the spring pins of the other PCB to create a stable electrical connection between the PCB of the microelectrode sensing device and the other PCB of the metal clamp. The system can include a welding clamp that includes insertion structures corresponding to the spring pins of the other PCB of the metal clamp arranged in vertical alignment with the spring pins. The welding clamp can include positioning structures corresponding to the positioning structures of the metal clamp.

In another aspect, a method for recording electrophysiological signals includes adding a cell suspension that includes multiple cells to a cell culture chamber of a microelectrode sensing device that includes at least one recording electrode and corresponding positioning electrodes. Experimental data is obtained by selectively applying positioning signals to one or more of the positioning electrodes to cause the cells in the cell suspension to form one or more cell patterns. The one or more recording electrodes are used to record electrophysiological signals associated with the cell patterns. Also, control data is obtained using the recording electrodes to record electrophysiological signals associated with the cells in absence of positioning signals. The obtained experimental data is compared with the obtained control data to identify an effect of selectively applying the positioning signals.

Implementations can optionally include one or more of the following features. Selectively applying the positioning signals can include selectively applying the positioning signals to all positioning electrodes. Selectively applying the positioning signals includes selectively applying the positioning signals to selective positioning electrodes. Selectively applying the positioning signals can include selectively applying the positioning signals continuously. Selectively applying the positioning signals can include selectively applying the positioning signals periodically.

The techniques, systems, and apparatus as described in this specification can optionally provide one or more of the following advantages. An electrode sensing device can be implemented as an array of positioning and sensing electrodes. Each electrode on the microelectrode sensing device can be operated separately to generate different cell patterns and detect an electrophysiological signal. At the same time, the microelectrode sensing device can complete other functions, such as cell electro-rotation.

Also, the microelectrode sensing device can include a chip unit, a printed circuit board (PCB) and a cell culture chamber. A substrate of the chip unit can be implemented using glass, and the positioning electrodes can be arranged in a ring for easy observation of the device under an inverted microscope. In addition, the microelectrode sensing device as described in this specification can be implemented to reduce crosstalk in electrodes, reduce noise and increase signal to noise ratio.

DETAILED DESCRIPTION

Micro-electrode arrays (MEAs) can be used for real-time electrophysiological measurement at the cellular tissue and system levels. A typical miniature microelectrode array can be used to monitor and record bioelectric activities of cultured cells, such as myocardial cells.

Because neurons cultured in vitro can not be easily positioned at or near the electrodes, an undesired spatial distance may exist between the neurons and the electrodes. Applying electrical stimulations and detecting electrophysiological signals are sensitive to the spatial relation between the neurons and the electrodes. In other words, the amplitudes of the detected electrophysiological signals become lower as the distance become larger.

Positioning cells in a microelectrode device can be accomplished by having micro-wells or micro-tunnels fabricated on the surface of MEAs through micro-fabrication techniques. However, such implementations require moving the neurons to the wells or tunnels through capillaries one by one. In addition, neurons may escape from the wells and tunnels.

Also, the surface of the MEAs can be modified using the differences between the adherence ability of neurons to different substrates to achieve positioning cells. However, beside the requirement of binding biological molecule to the substrate, getting the molecule positioned accurately is difficult, and the modified MEAs can not be used again.

Techniques, systems, and apparatus are provided for positioning cells at or near the recording or sensing electrodes in a microelectrode sensing device. The ability to position the cells at a desired location can enhance the detection ability of MEAs and increase the applicable fields for the MEAs. The same microelectrode sensing device includes recording electrodes for recording bioelectrical activities of the positioned cells.

Figure 1:
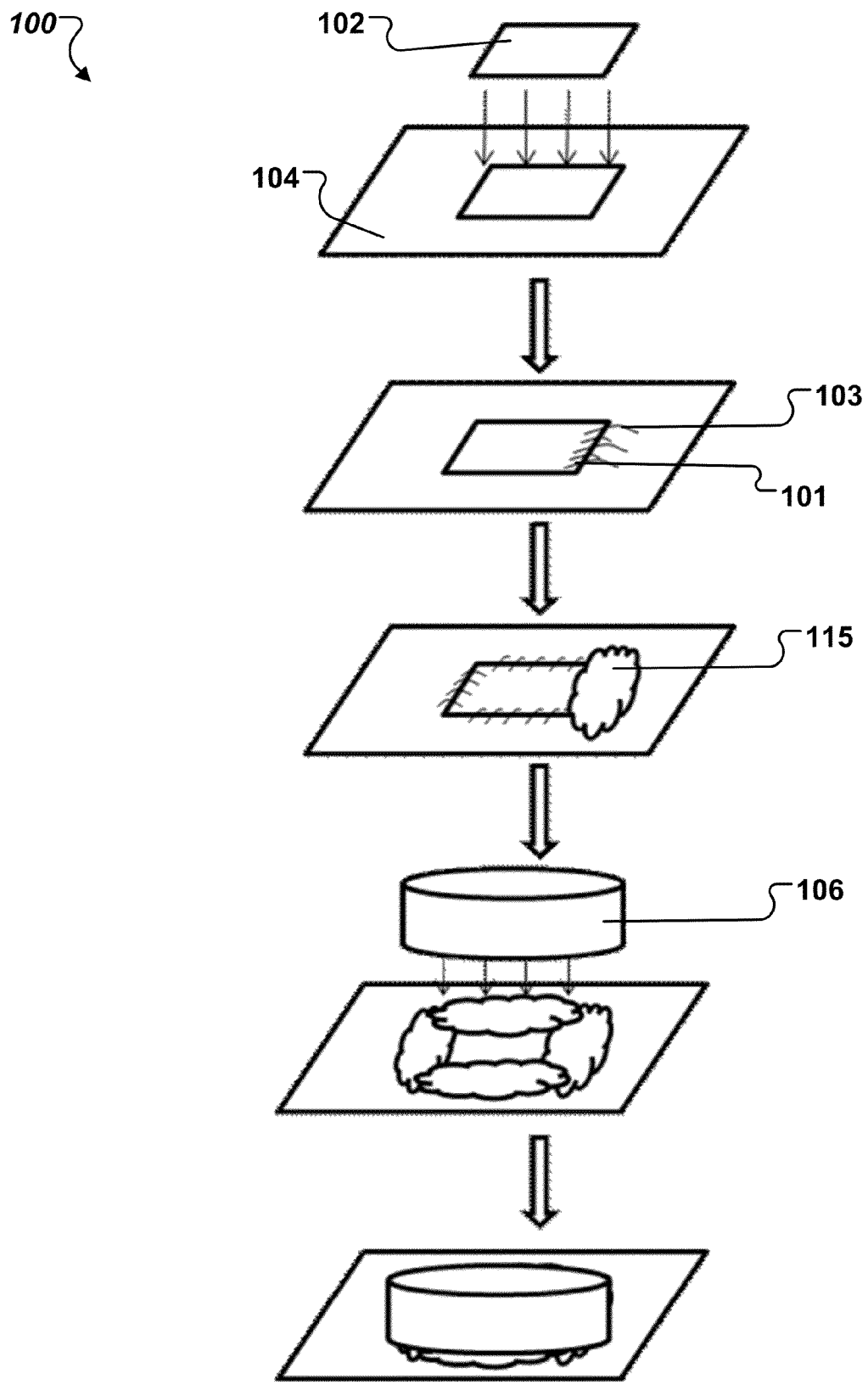
FIG. 1 shows an example process of assembling microelectrode sensing device.

FIG. 1 shows an example process of assembling a microelectrode sensing device. A microelectrode sensing device 100 includes a chip unit 102, a printed circuit board (PCB) 104, and a cell culture chamber 106. The chip unit 102 is assembled to the PCB 104 by wire bonding the chip unit 102 to the PCB 104. In addition, the wire bonded chip unit 102 is inserted inside the cell culture chamber 106. The chip unit 102 is sealed between the PCB 104 and the cell culture chamber 106.

To encapsulate the microelectrode sensing device, the chip unit 102 is assembled to the PCB 104. Then, pads on both the chip unit 102 and the PCB 104 are connected using conductive materials such as spun gold 101 and 103. For example, spun gold 103 is connected to outer row of pads of the PCB 104, and spun gold 101 is connected to inner row of pads of the PCB 104. The spun gold 103, 101 are protected by silica resin 115. The chip unit 102 is located inside the cell culture chamber 106 with the cell culture chamber 106 sealed to the PCB 104. The cell culture chamber 106 can be sealed to the PCB 104 using silica resin or similar adhesives.

Figure 2:
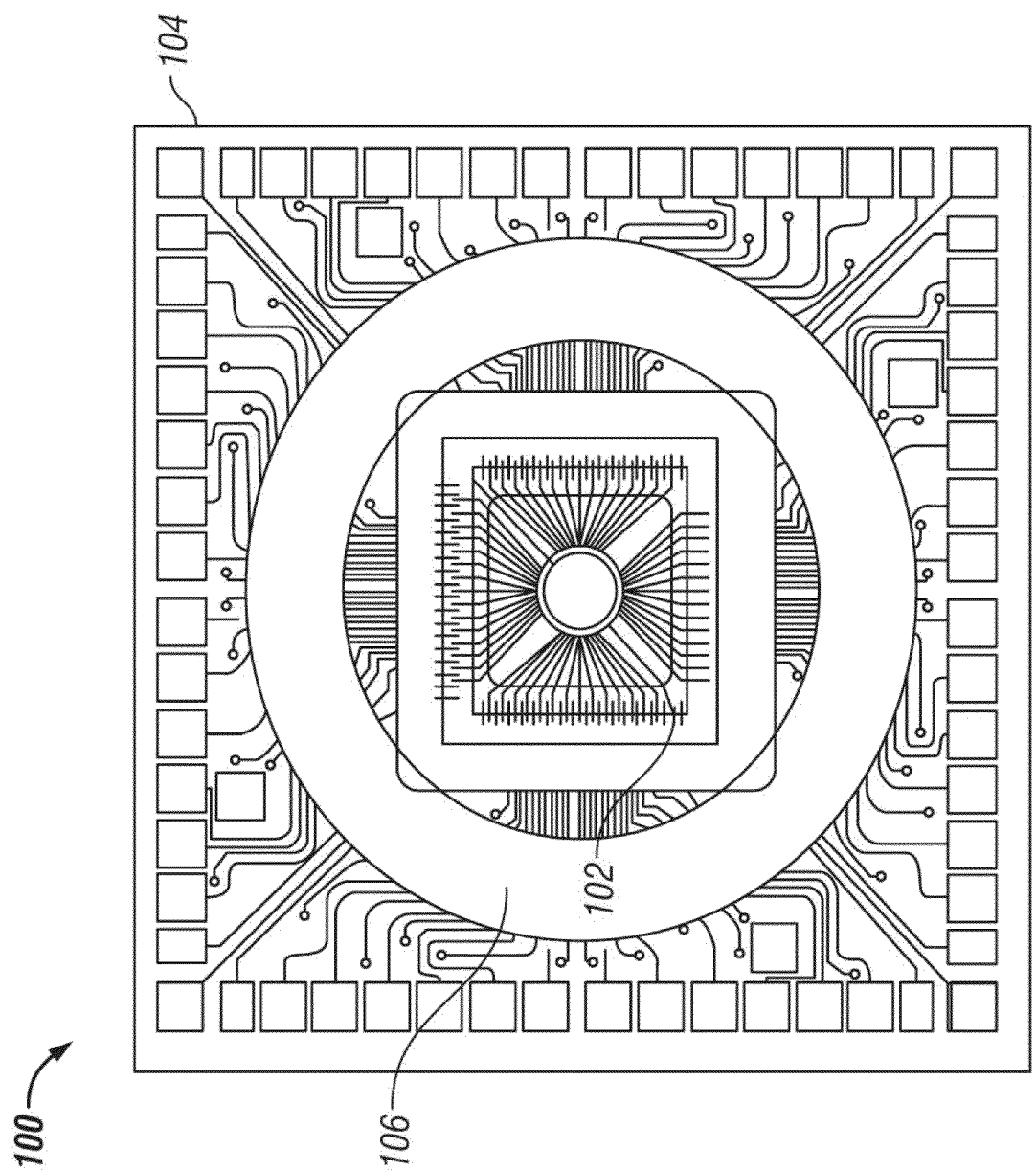
FIG. 2 shows an example of an assembled microelectrode sensing device.

FIG. 2 shows an example of an assembled microelectrode sensing device. As described above, the microelectrode device 100 includes a chip unit 102, a PCB 104 and a cell culture chamber 106. A chip unit 102 is attached to a PCB 104 and enclosed inside a cell culture chamber 106.

Figure 3A:
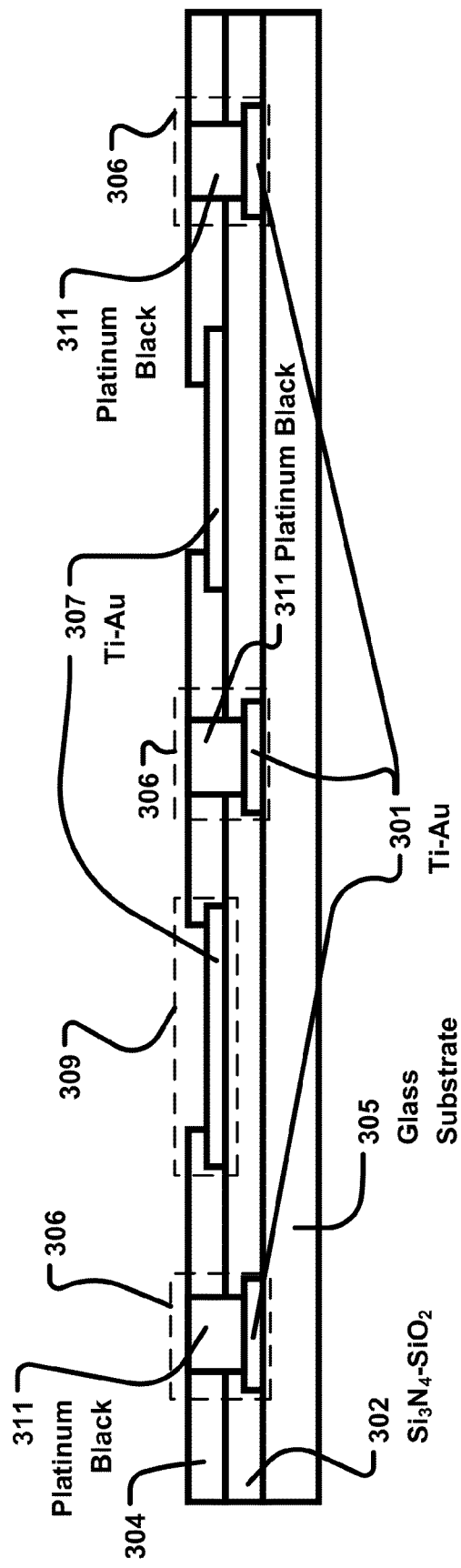
FIG. 3a shows a cross-sectional view of electrodes area of an example chip unit.
Figure 3B:
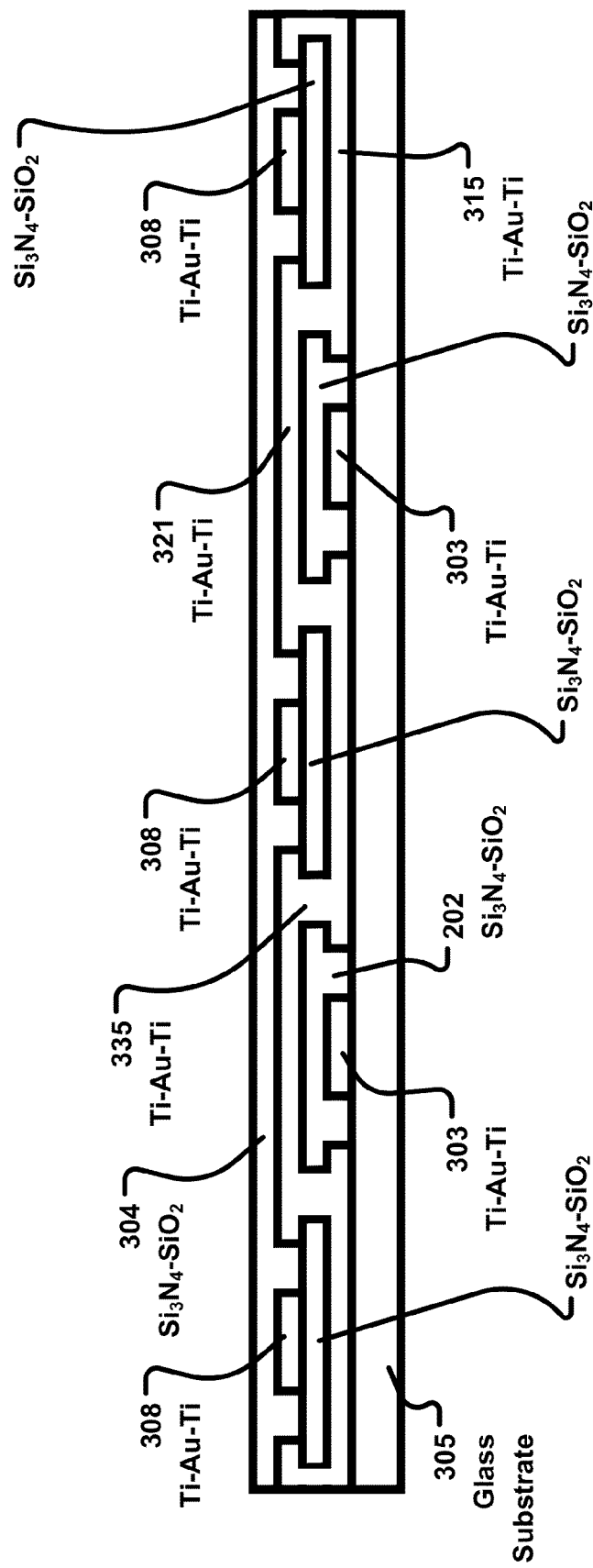
FIG. 3b shows a cross-sectional view of a wire area of an example chip unit.

FIGS. 3a and 3b show example layers of a chip unit in a microelectrode sensing device. The chip unit (e.g., chip unit 102) includes multiple layers, such as a substrate layer 305, a first conductive layer 301, a first insulation layer 302, a second conductive layer 307, and a second insulation layer 304. The insulation layers can include two different layers of $Si_3N_4$ and $SiO_2$.

The first conductive layer can include one or more recording electrodes 306, interconnects (i.e., wires) 303 and pads. The surfaces of the recording electrodes 306 are electroplated with a layer spongy material, such as platinum black 311. The second conductive layer includes four or more positioning electrodes 309, wires 308, and pads.

Each of the recording and positioning electrodes is separately linked to a pad, such as a bond pad. Also, signals can be applied to each electrode independent of other electrodes. Similarly, each electrode can be used to detect bioelectric activities separate and independent of the other electrodes.

To improve cell positioning effect and increase the signal to noise ratio, the microelectrode sensing device can be optimized by turning the wires 303, 308 using arcs. Thus, all wires have rounded corners. Also, the wires 303 and 312 (see FIG. 5a below) can be gradually widened from the recording electrodes 306 to the pads. Further, the ground electrodes 315 and 321 can be placed at both conductive layers 301 and 307. The ground electrodes 315 and 321 can be connected through a passage 335 at the first insulation layer 302 to ensure that any two wires 303 and 308 can be separated by ground electrodes 315, 321 and 335.

In addition, to reduce attenuation of crosstalk in electrodes, reduce noise and increase signal to noise ratio, the chip unit 102 can be optimized in design. For example, many ground electrodes can be fabricated on the conductive layers, and these ground electrodes can be connected through passages in the first insulation layer. Thus, each wire that links an electrode to a pad can be separated by ground electrodes.

To facilitate viewing or imaging of the microelectrode device under an inverted microscope the substrate of the chip unit 102 can be implemented to include glass. In addition, the positioning electrodes 309 can be arranged in a ring.

Fabrication of a Chip Unit.

Figure 4:
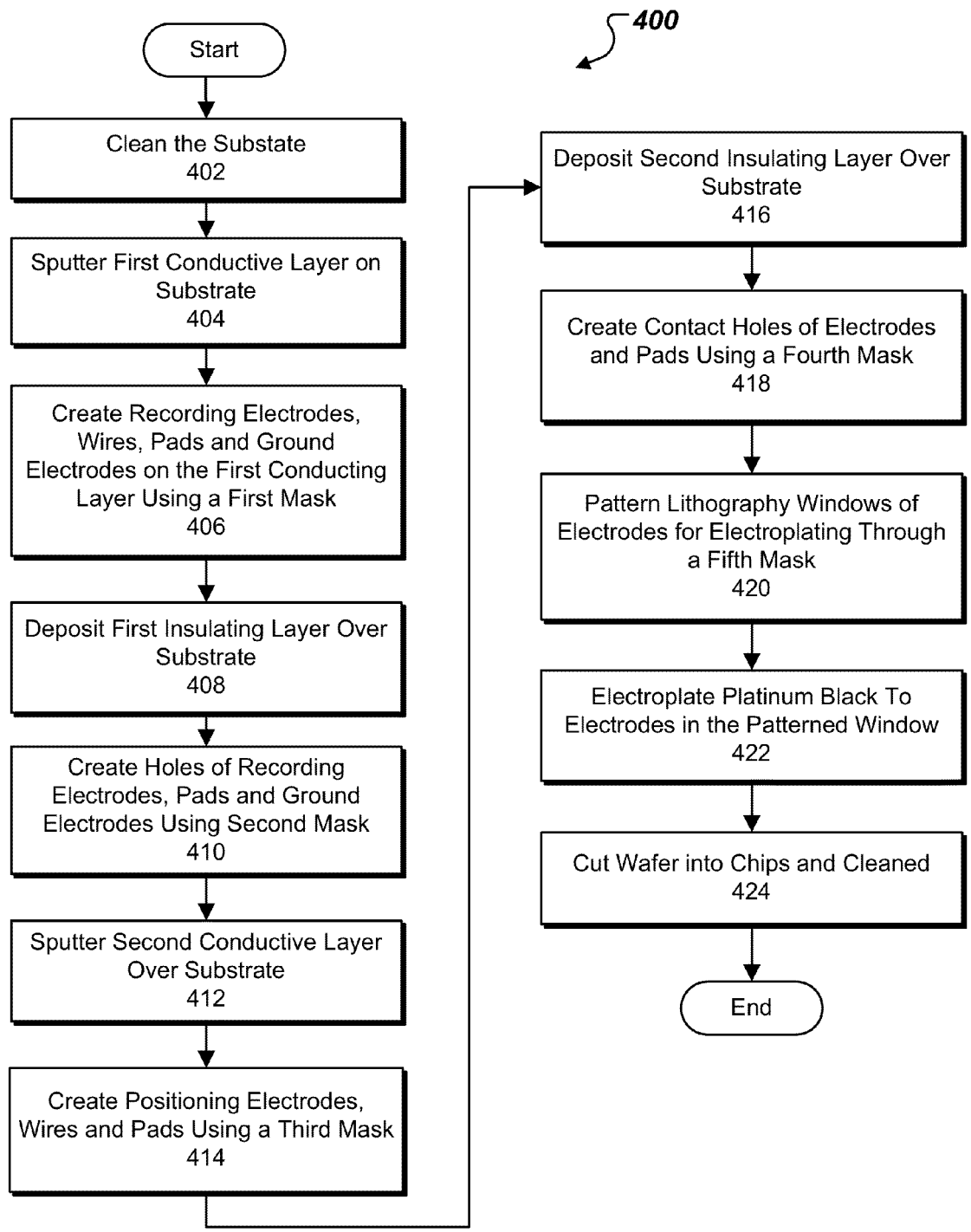
FIG. 4 shows an example process of chip unit microfabrication.

FIG. 4 shows an example process 400 for fabricating a chip unit. A substrate is cleaned (402). The first conductive layer (e.g., Ti—Au—Ti) is sputtered on the cleaned substrate (404). Recording electrodes, wires, pads, and ground electrodes are created on the conductive layer using a first mask (406). For example, recording electrodes, wires, pads, and ground electrodes can be patterned by photolithography through mask A, shown in FIG. 5a below, and etched. A first insulation layer is deposited over the substrate including the first conductive layer (408). For example, an insulation layer of Si3N4-SiO2 can be deposited on the substrate using PECVD. The contact holes of recording electrodes, pads, and ground electrode passages are created in the first insulation layer using a second mask (410). For example, the contact holes can be patterned through mask B, shown in FIG. 5b below, and etched. A second conductive layer is created over the substrate including the first conducting layer and the first insulation layer (412). For example, a conductive layer of Ti—Au—Ti can be sputtered over the first insulation layer.

Positioning electrodes, wires, and pads are created on the second conductive layer using a third mask (414). For example, positioning electrodes, wires, pads, and ground electrodes can be patterned through mask C, shown in FIG. 5c below, and etched. A second insulation layer is deposited over the substrate including the first conductive layer, the first insulation layer, and the second conductive layer (416). For example, an insulation layer of $Si_3N_4$—$SiO_2$ can be deposited on the substrate using PECVD and be in contact with the first insulation layer. The contact holes of positioning electrodes, recording electrodes, pads, and ground electrodes are created using a fourth mask (418). For example, the contact holes of positioning electrodes, recording electrode, pads, and ground electrodes can be patterned through mask D, shown in FIG. 5d, and etched. The windows of electrodes for electroplating are patterned using a fifth mask, such as mask E shown in FIG. 5E below (420).

A layer of platinum black is applied to the windows of electrodes (422). Each window patterned by the fifth mask indicates an area used to mark the electrode for applying platinum black. In other words, all electrodes located inside the patterned window are electroplated with platinum black. For example, platinum black can be electroplated to the electrodes located inside the windows by applying a constant current utilizing an ultrasonic agitation. The wafer is cut into chips and cleaned (424).

Figure 5A:
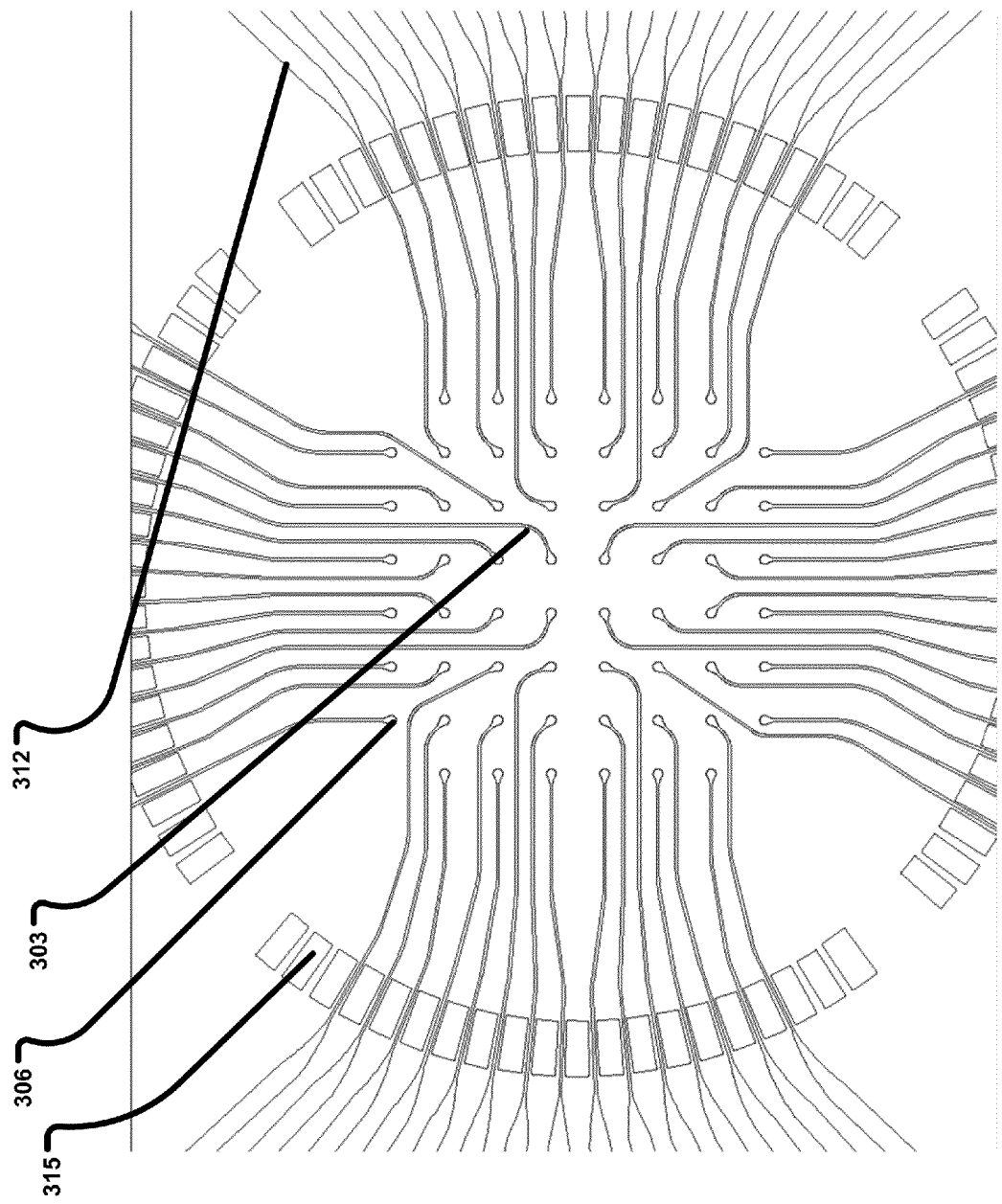
FIGS. 5a-e show mask designs of each layer on a chip unit.
Figure 5B:
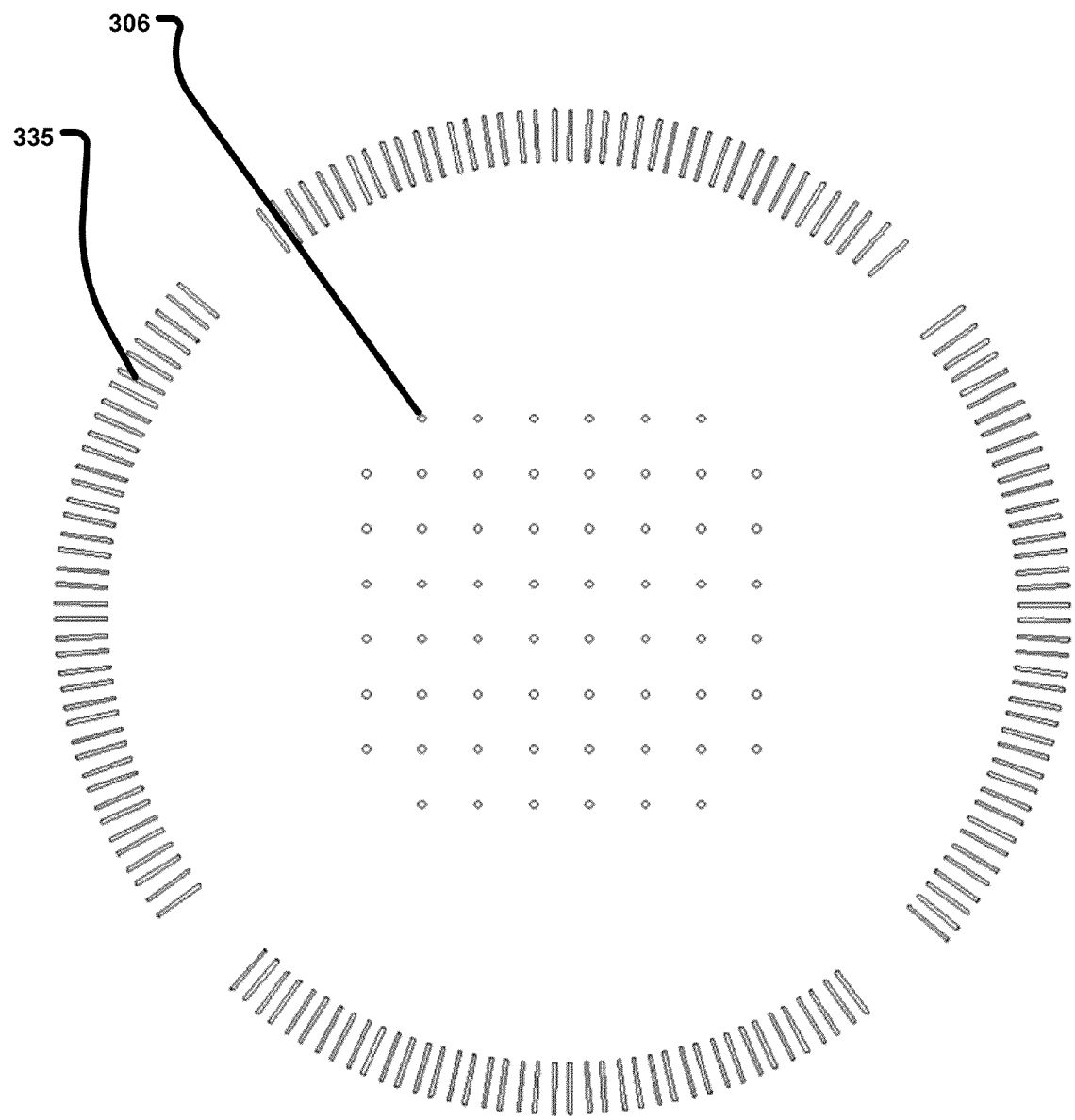
Figure 5C:
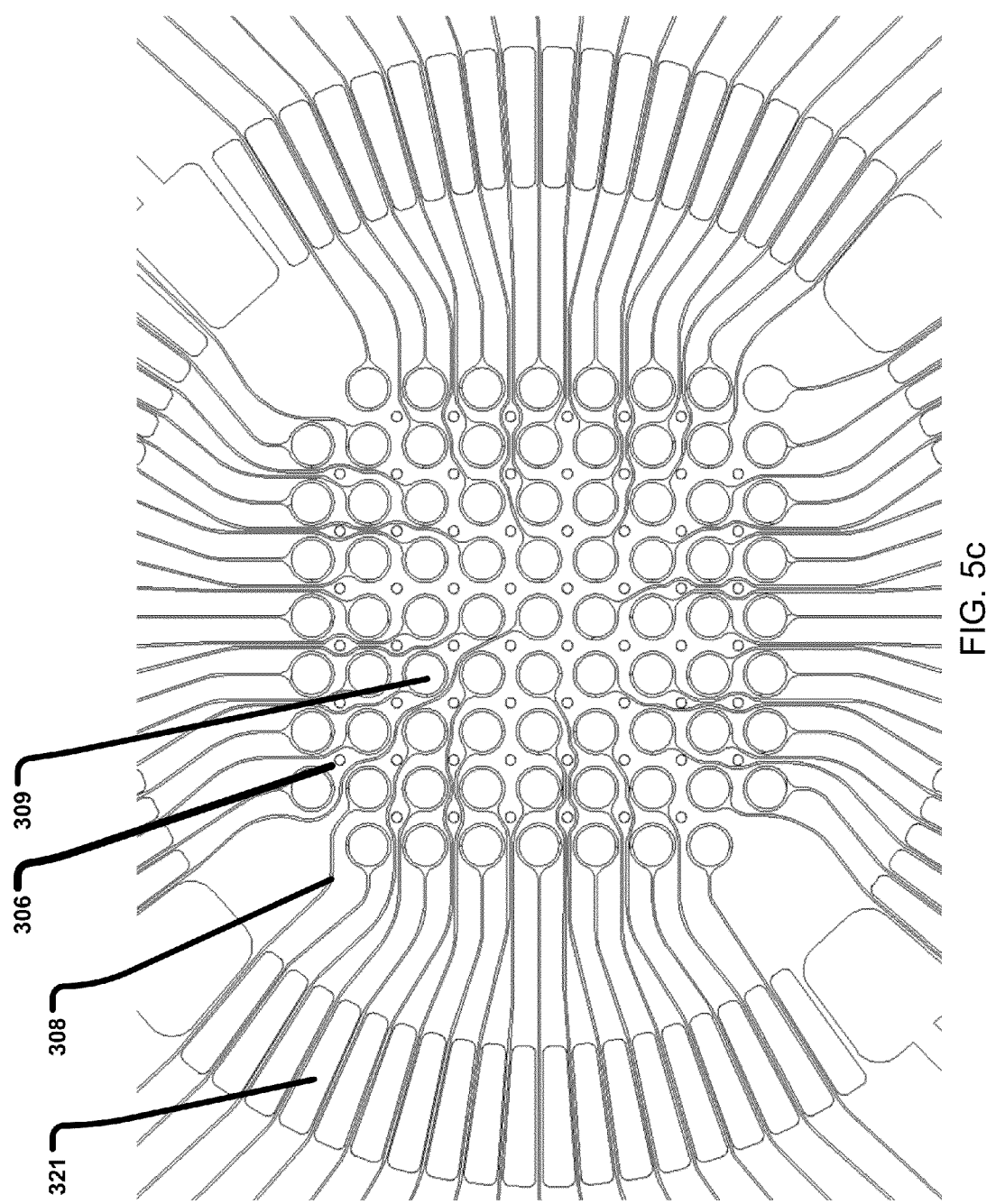
Figure 5D:
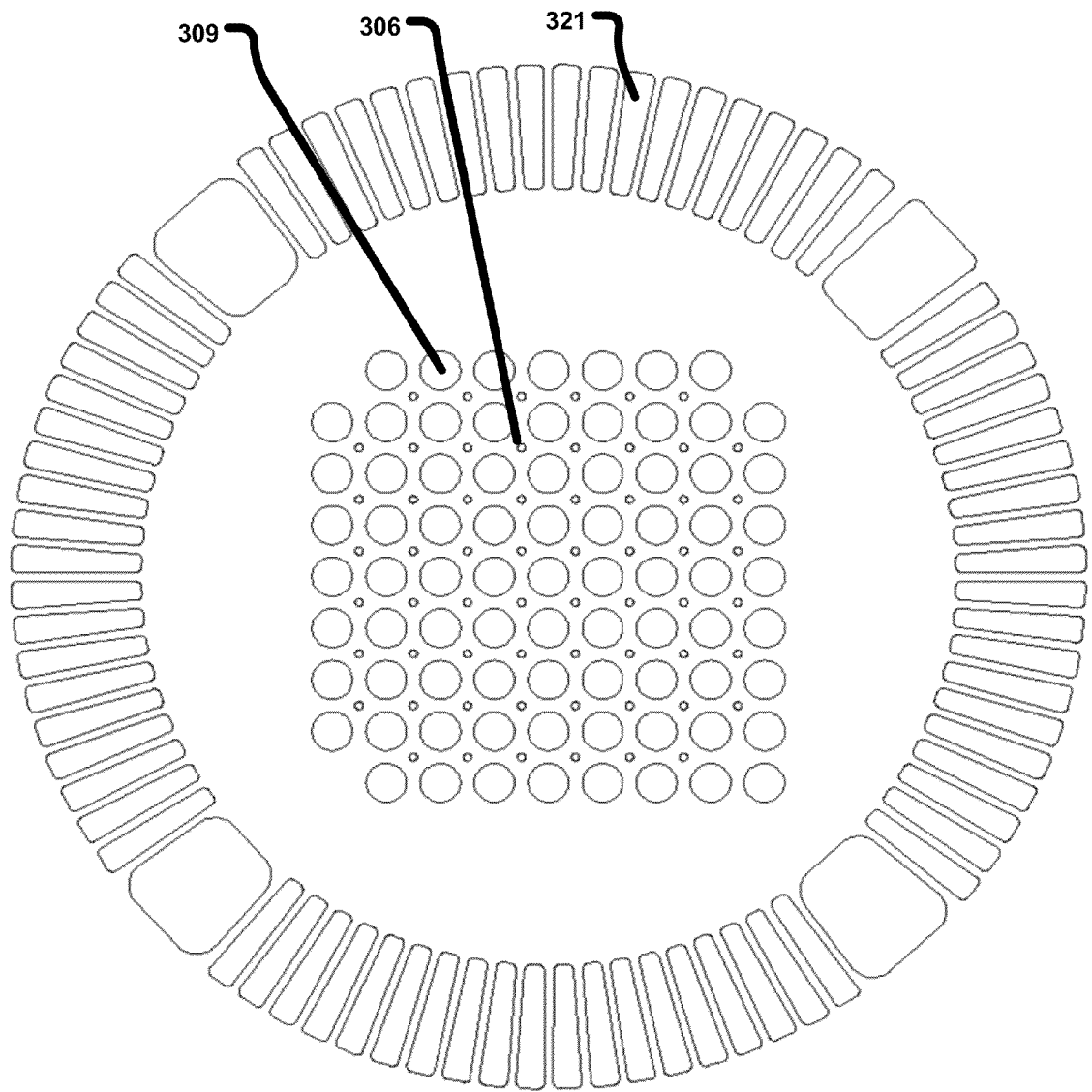
Figure 5E:
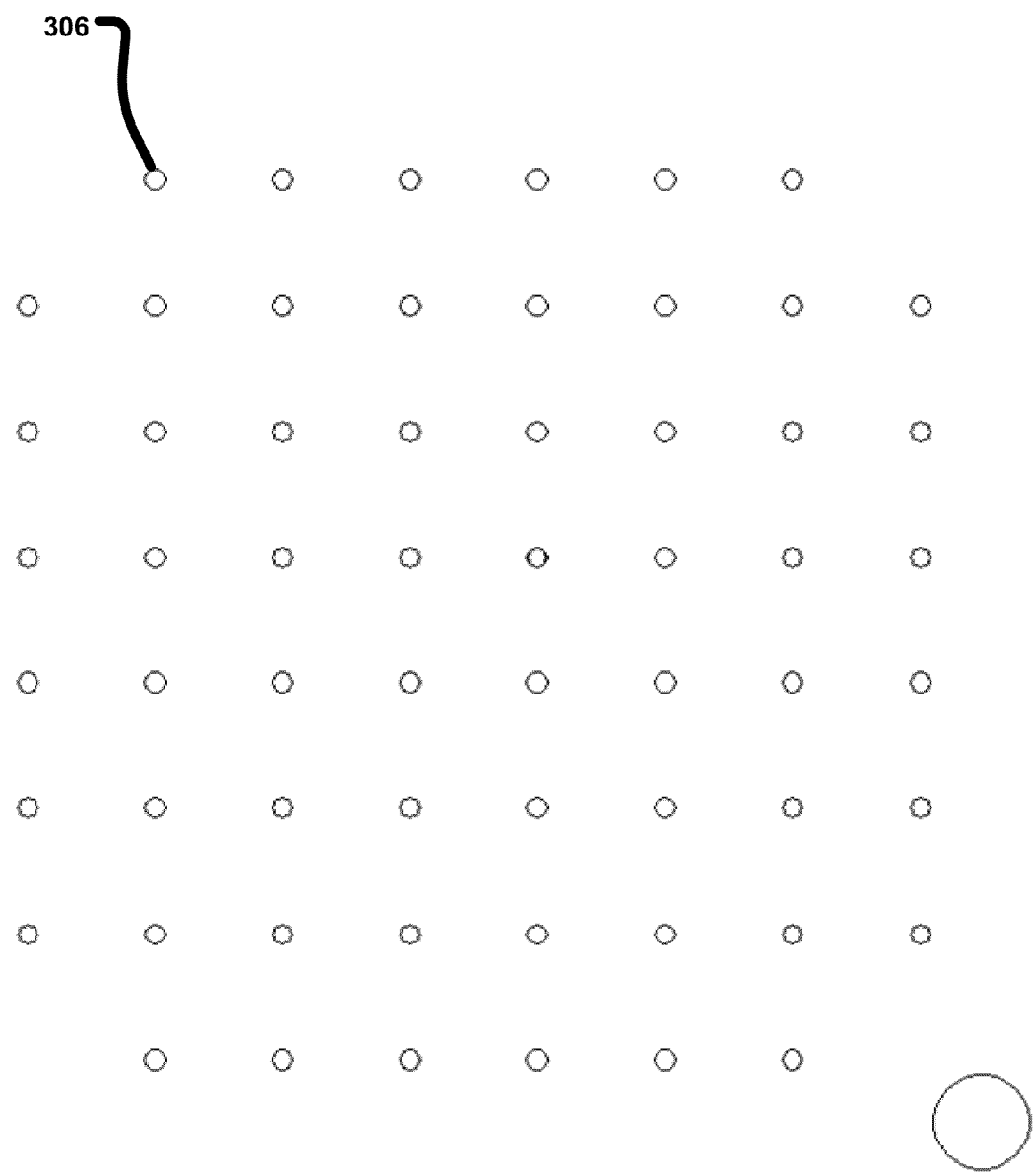

FIG. 5a, 5b, 5c, 5d, and 5e show various masks used to fabricate a chip unit. FIG. 5a shows a mask for etching recording electrodes (e.g., recording electrodes 306), wires (e.g., wires 303/312), pads (not shown in this figure), and ground electrodes (e.g., ground electrodes 315). FIG. 5b shows a mask for etching (wet and dry) recording electrodes (e.g., recording electrodes 306), pads, and ground electrode passages (e.g., ground electrode passages 335) using lithography. FIG. 5c shows a mask for etching positioning electrodes (e.g., positioning electrodes 309), recording electrodes (e.g. recording electrodes 306), wires (e.g. wires 308), pads (not shown in this figure), and ground electrodes (e.g., ground electrodes 321) using lithography. FIG. 5d shows a mask for etching (wet and dry) positioning electrodes (e.g. positioning electrodes 309), recording electrodes (e.g., recording electrodes 306), pads (not shown in this figure), and ground electrodes (e.g., ground electrodes 321) using lithography. FIG. 5e shows a mask for generating lithography windows of electrodes for electroplating platinum black onto the recording electrodes for example.

PCB of a Microelectrode Sensing Device

Figure 6A:
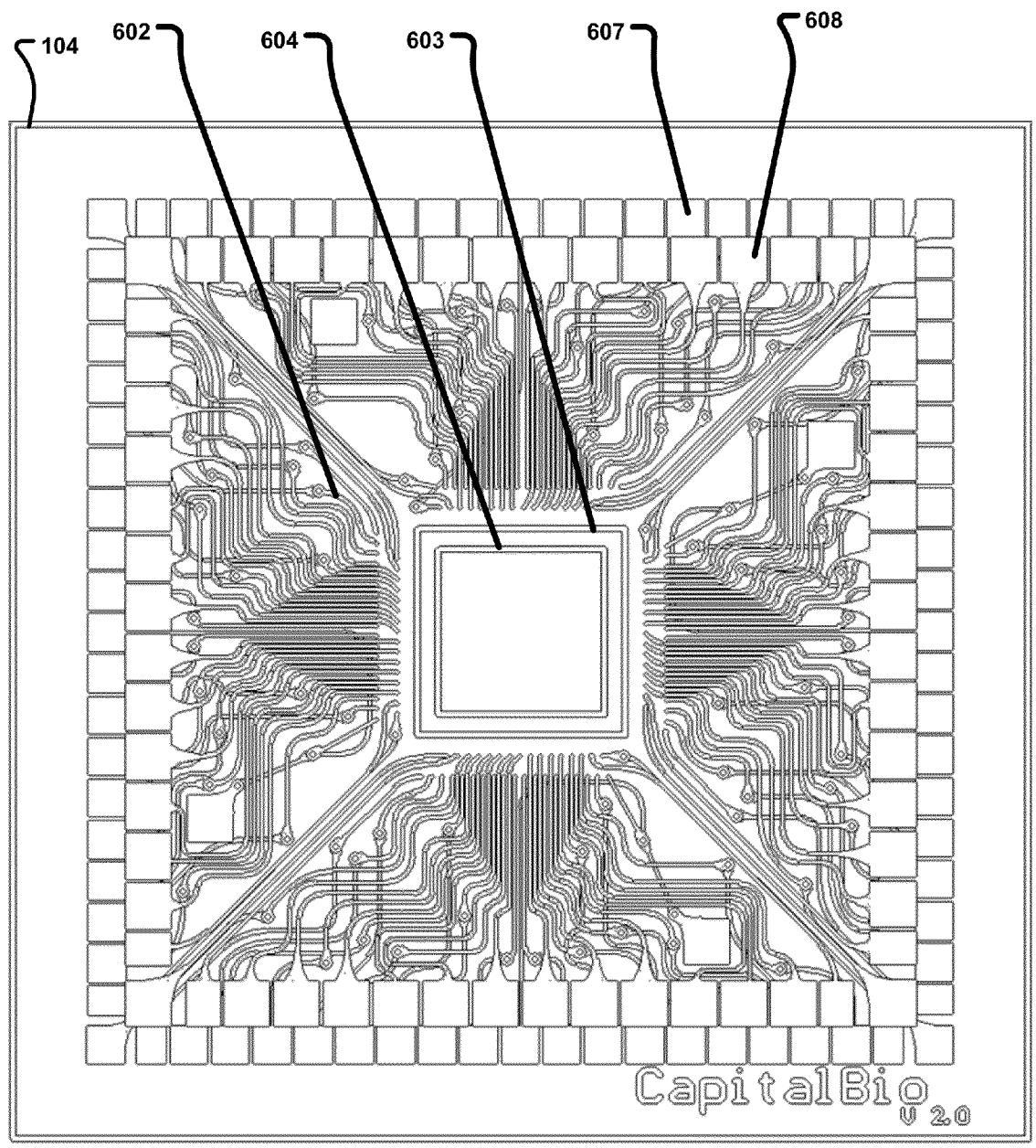
FIG. 6a shows an example of a PCB design of a microelectrode sensing device.
Figure 6B:
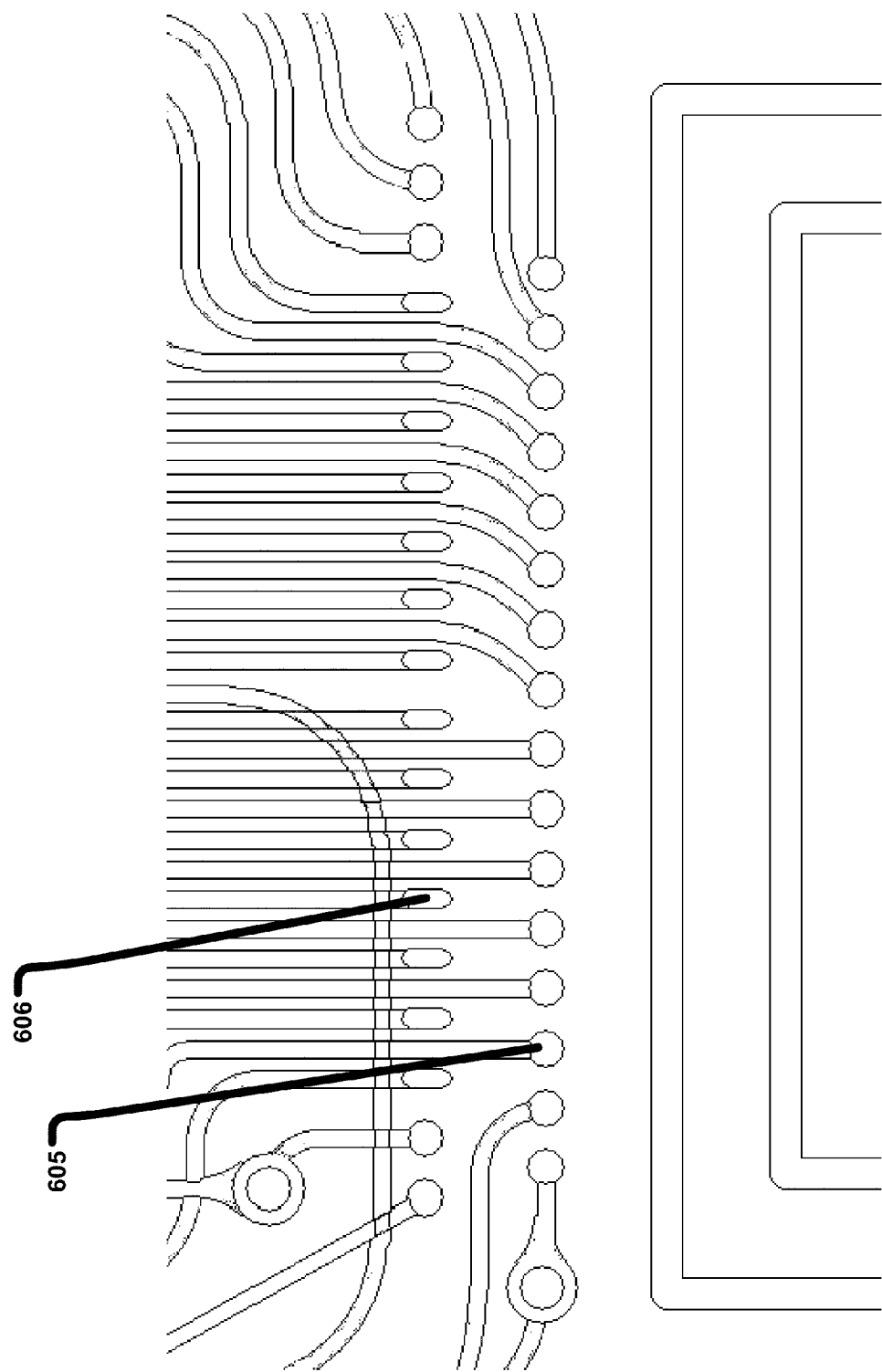
FIG. 6b shows an enlarged view of example pads.

FIGS. 6a and 6b show an example PCB. The PCB (e.g., PCB 104) includes a carved out center area 604 for facilitating observation under an inverted microscope. The chip 102 is assembled to the area indicated by 603. The PCB also includes pads 605 and 606 that surround the carved out center area 604 near the inner region of the PCB. Also, additional pads 607, 608 are located near the outer edge of the PCB and surround the pads 605 and 606. The PCB also includes wires 602 for connecting pads 605 or 606 of the PCB to the pads 607 or 608 on the same PCB. The wires 602 that connect the inner pads 605, 606 with outer pads 607, 608 are shaped as arcs. The pads 605 and 606 of the PCB can include two types of pads arranged in two pad areas. For example, the two types of pads can be arranged in alternating positions, such as two rows. For example, pads 605 represent an inner row of pads. Pads 606 represent an outer row of pads.

To facilitate bonding and increase bonding efficiency, two types of pads 605 and 606 are provided on the PCB at two pad areas. For example, at one pad area (e.g., an inner row), the pads 605 are shaped as circles. At another pad area (e.g., an outer row), the pads 606 are shaped as rectangles. Other shapes and arrangement can be implemented. Also, the wires 602 connecting the pads at inner brim of PCB to the pads at outer brim of PCB have rounded corners to increase the signal to noise ratio. The pads on the chip unit can be distributed at the edge of chip equably.

Figure 7A:
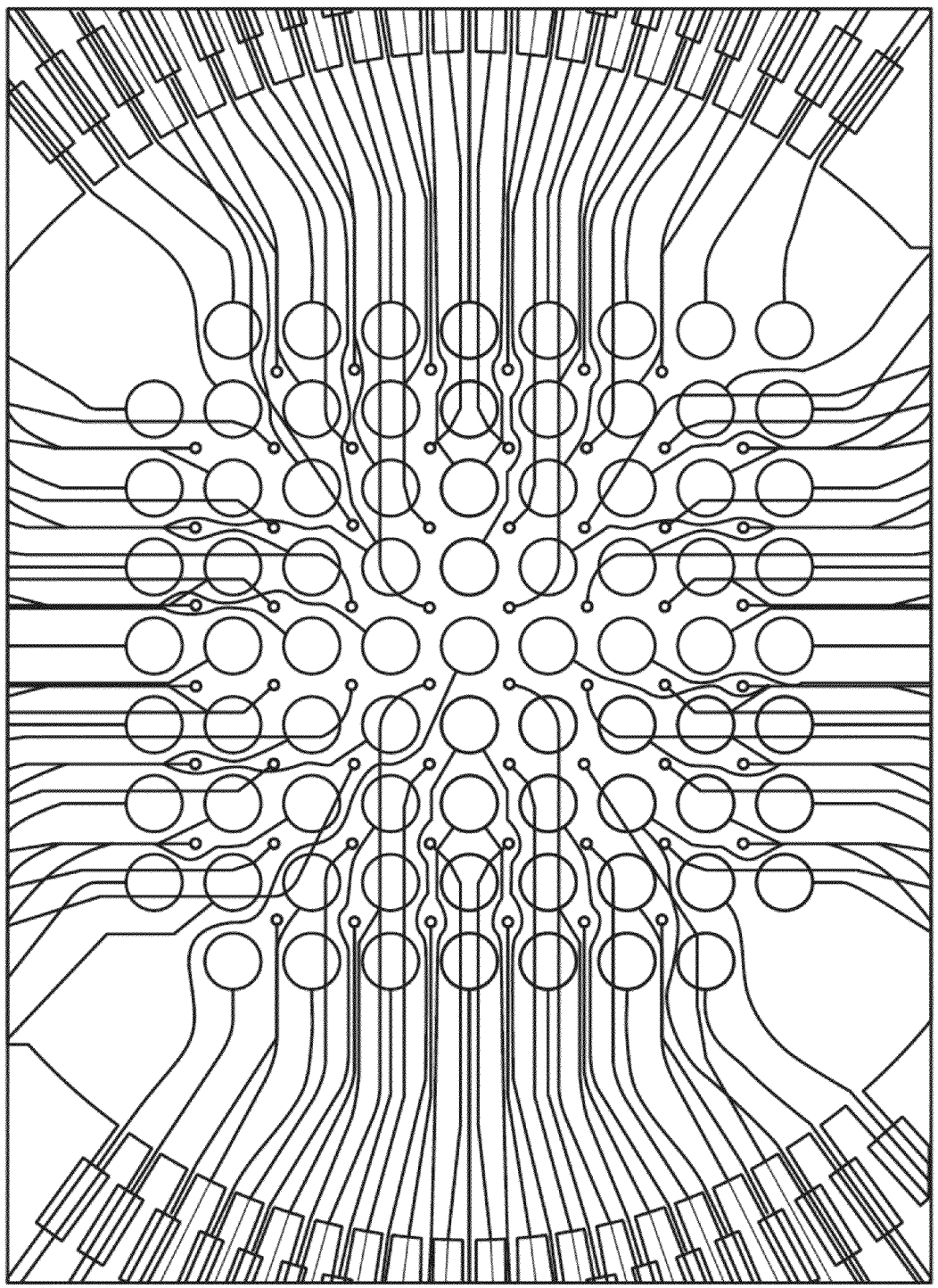
FIG. 7a is a picture captured from under an upright microscope showing electrodes of an example microelectrode sensing device.
Figure 7B:
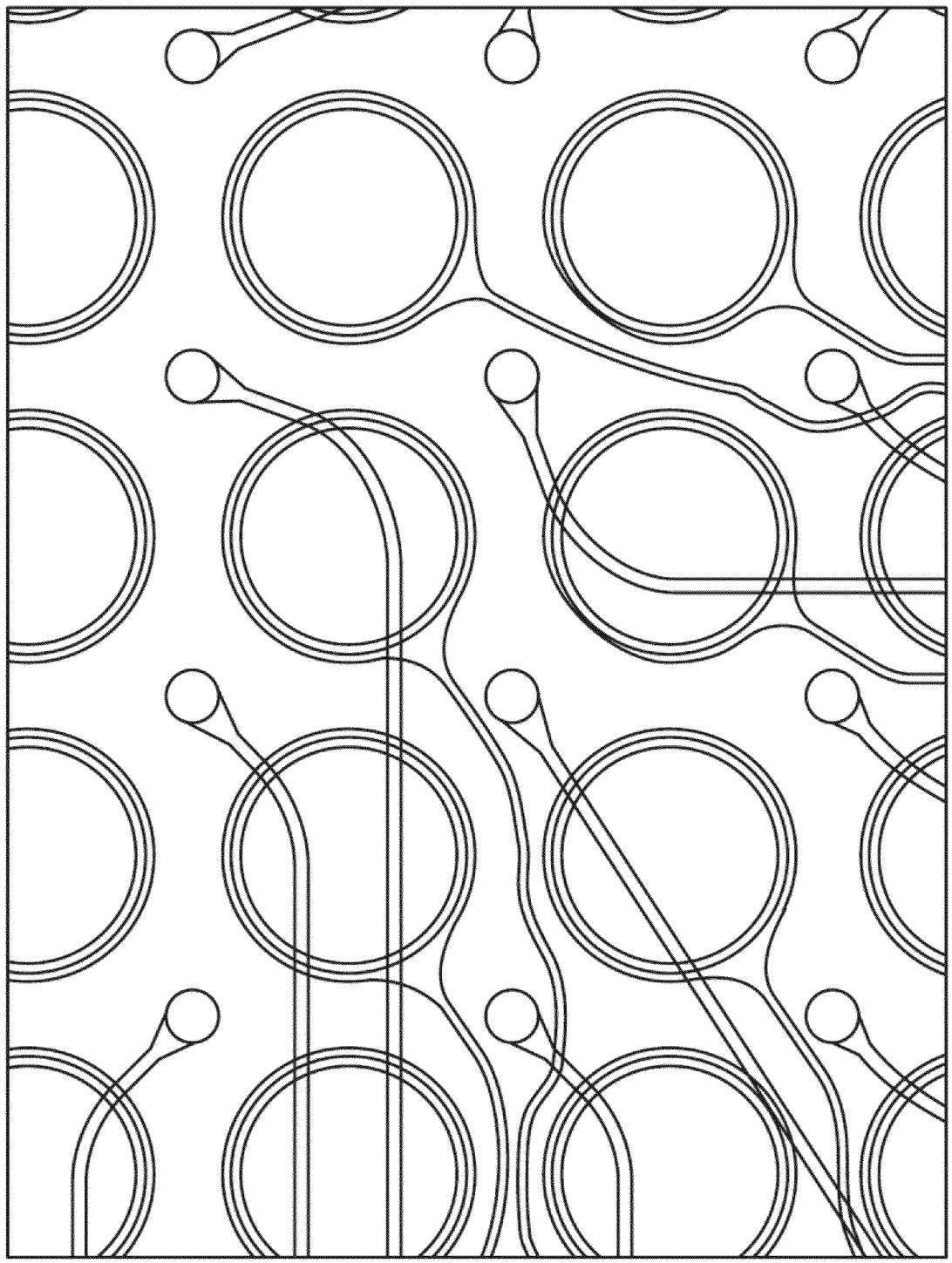
FIG. 7b shows an enlarged view of electrodes in an example microelectrode sensing device.

As described above, the microelectrode sending device can be designed and assembled for easy viewing under an inverted microscope. FIG. 7a shows an example picture of a microelectrode sensing device captured under an upright microscope. The picture of the microelectrode sensing device shows all of the positioning and recording electrodes. FIG. 7b shows an enlarged version of the picture shown in FIG. 7a.

Figure 8A:
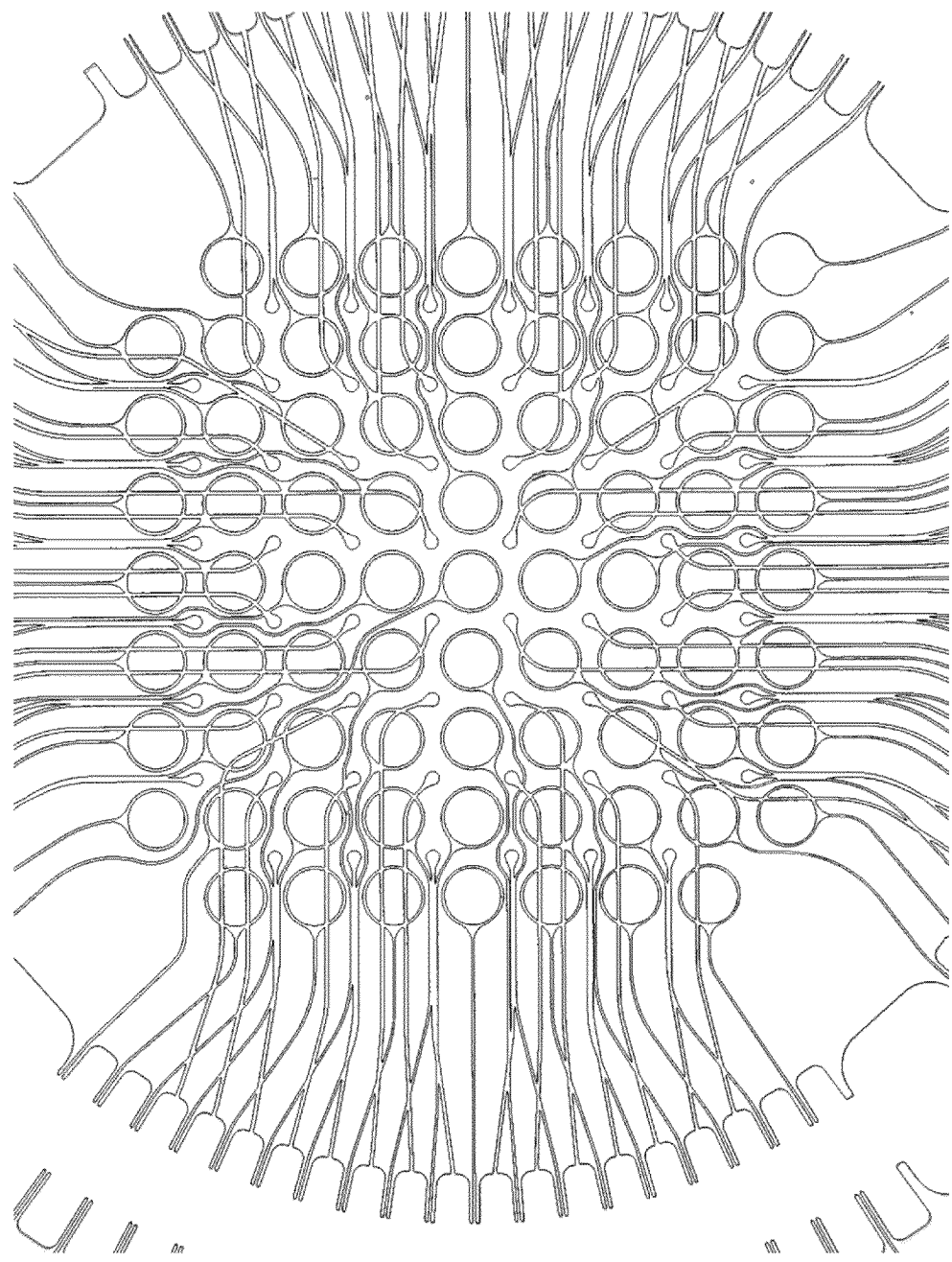
FIG. 8a is a picture captured from under an inverted microscope that shows electrodes of an example microelectrode sensing device.
Figure 8B:
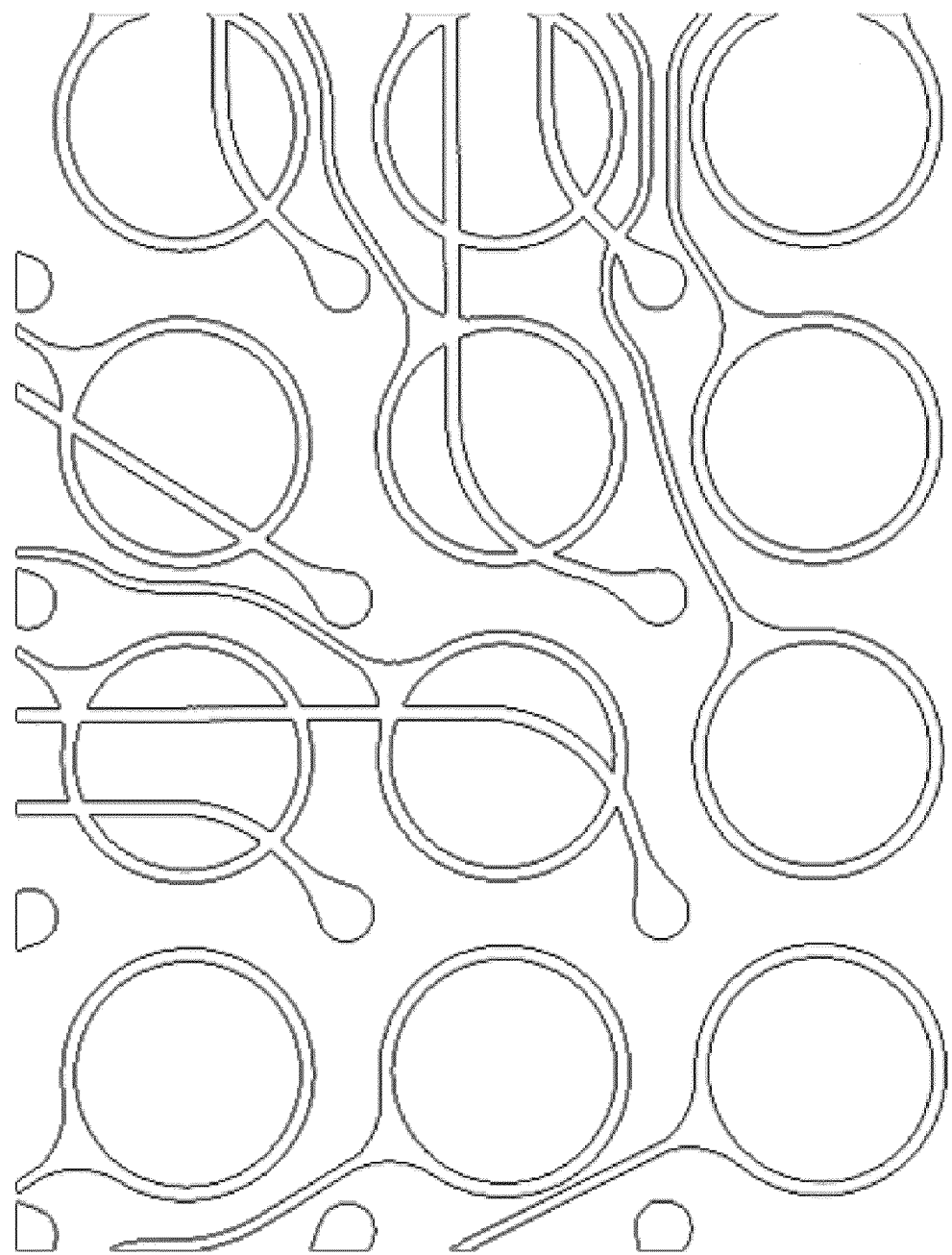
FIG. 8b shows an enlarged view of electrodes in an example microelectrode sensing device.

FIG. 8a shows another example picture of a microelectrode sensing device including all of the recording and positioning electrodes. FIG. 8b shows an enlarged version of FIG. 8a. The design of the microelectrode sensing device shown in FIGS. 8a-8b provides a larger observable area under an inverted microscope.

Example Device for Cell Manipulation

Figure 9:
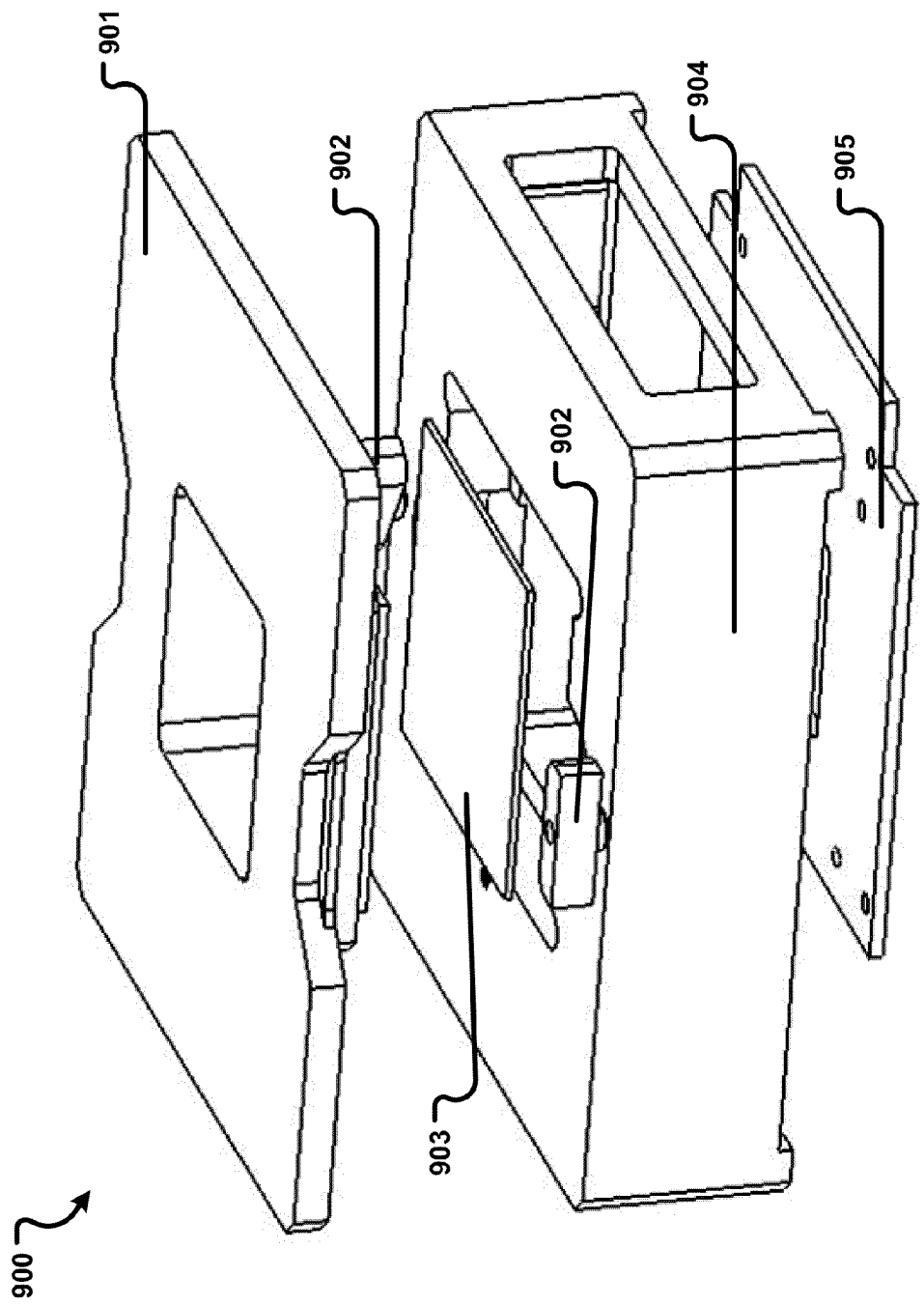
FIG. 9 shows an assembly of an example metal clamp.

FIG. 9 shows an example device for performing cell manipulation electrophysiological detection. The device 900 used for cell manipulation includes a microelectrode sensing device 903 connected to a metal clamp. The metal clamp includes a PCB 905 with spring pins, a metal enclosure 904 and a cover plate 901. The PCB 905 for the metal clamp is different from the PCB attached to the chip unit. The PCB 905 with spring-pins is attached or connected to the metal enclosure 904. The spring-pins are used to apply signals to the chip unit. Two electrical connections are implemented to apply the signals to the chip unit. Using bonding, an electrical connection is provided between the chip unit 102 and the PCB 104 attached to the chip unit. Another electrical connection is provided between PCB 104 attached to the chip unit and the PCB 905 of the clamp using the spring-pins. The PCB 905 can include at least 3 positioning holes that can be used to firmly attach the PCB 905 to the metal enclosure 904. In use, the microelectrode sensing device 903 is placed on the spring-pins and pressed tightly by the cover plate 901 through two spanners 902. Also, the spring-pins on the PCB 905 are used to connect the PCB 905 of the metal clamp with the PCB 104 of the microelectrode sensing device 903.

The microelectrode sensing device 903 used for cell manipulation and electrophysiological detection includes a chip unit, a PCB, and a cell culture chamber. Thus, the microelectrode sensing device 903 can be fabricated to be the same as the microelectrode sensing device 100.

The cover plate 901 is used to fix the microelectrode sensing device 903 into the metal clamp. The cover plate 901 also ensures a steady connection between the two PCBs. The metal enclosure 904 includes a guide-path (shown in FIG. 11 below) corresponding to the microelectrode sensing device 903 to restrict the movement of the microelectrode sensing device 903 in the direction of the spring-pins.

Figure 10:
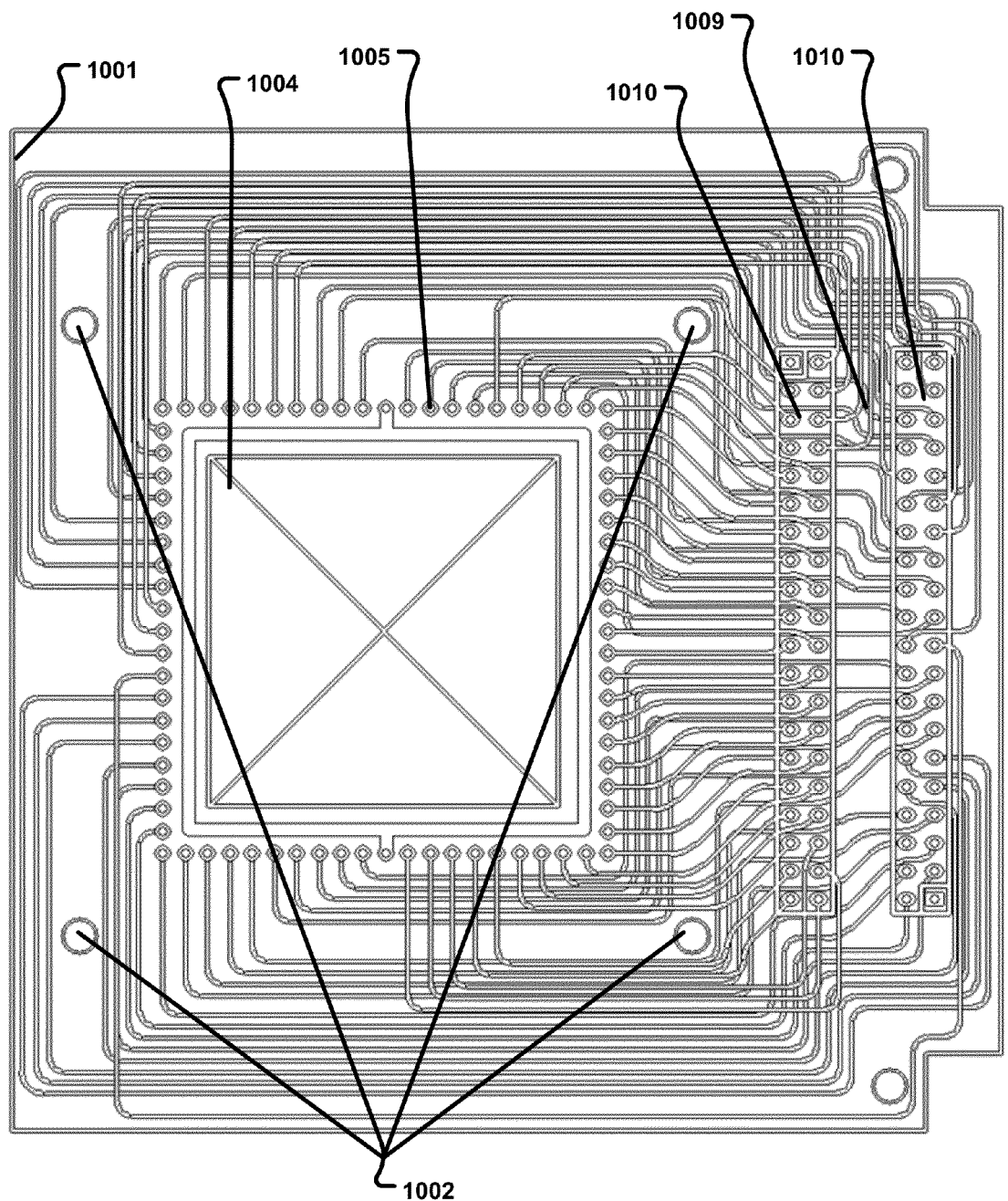
FIG. 10 shows a PCB design of an example metal clamp.

FIG. 10 shows an example PCB design for a metal clamp. The reference number 1001 represents a brim of a PCB for a metal clamp. The PCB for the metal clamp includes positioning holes 1002 used for fixing the PCB to a metal enclosure (e.g., metal enclosure 904). The PCB includes a window 1004 used for observing an attached microelectrode sensing device under a microscope. Also, the PCB includes pads 1005 of spring-pins. In addition, the PCB includes electrical outlets 1010 for attached cables to them. Further wires 1009 provide various interconnects in the PCB. The wires are implemented to have rounded corners, such as an arc.

Figure 11:
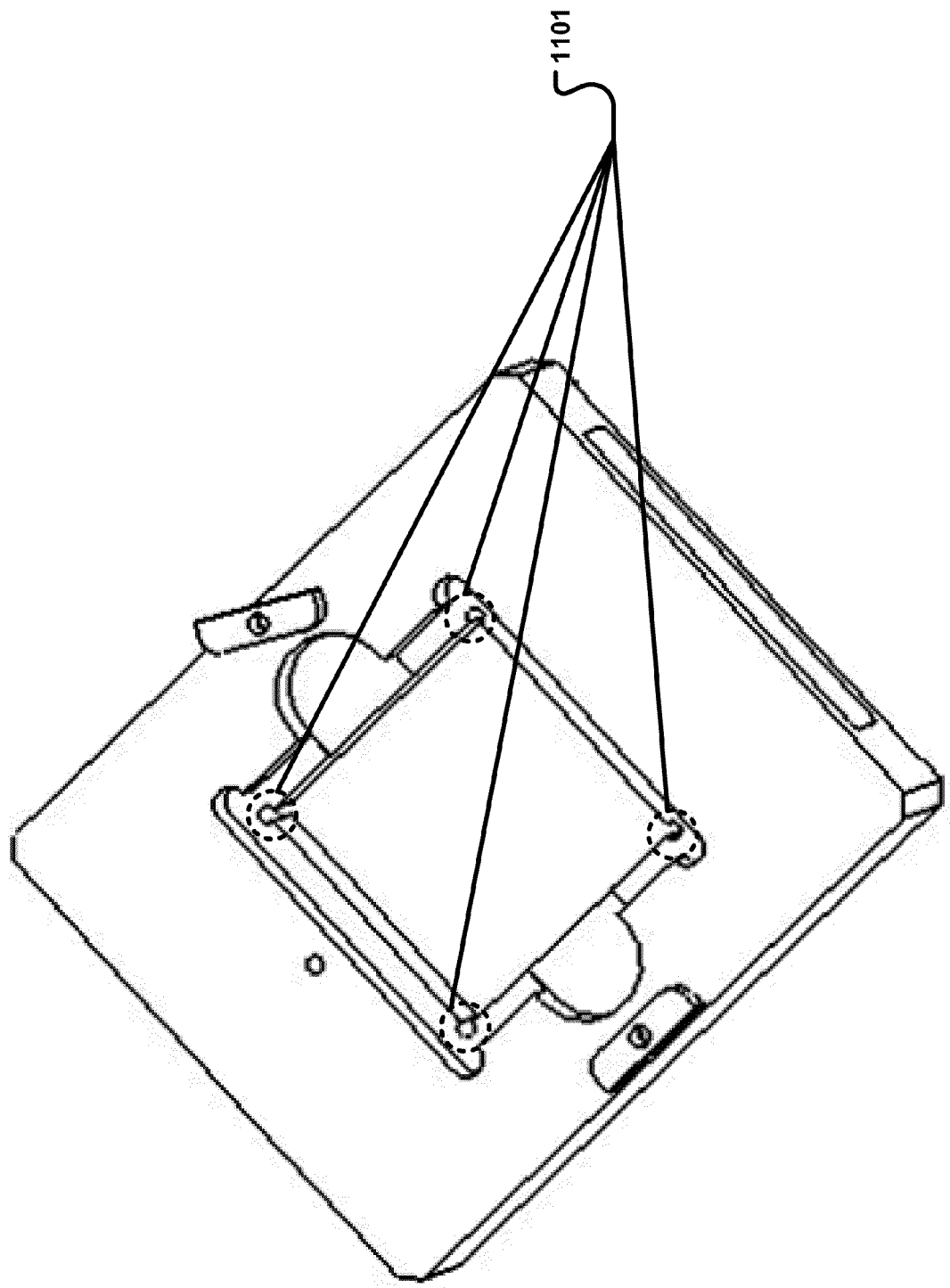
FIG. 11 shows a sketch map of a guide-path of an example metal clamp.

FIG. 11 shows an example of a guide-path on a metal enclosure of a metal clamp. As described with respect to FIG. 9 above, a metal enclosure includes guide-paths 1101 that correspond to a microelectrode sensing device to restrict the movement of the microelectrode sensing device 903 in the direction of the spring-pins. Also, guide-paths 1101 ensure that the pads of the microelectrode sensing device match with the spring-pins of the PCB of the metal clamp.

Figure 12:
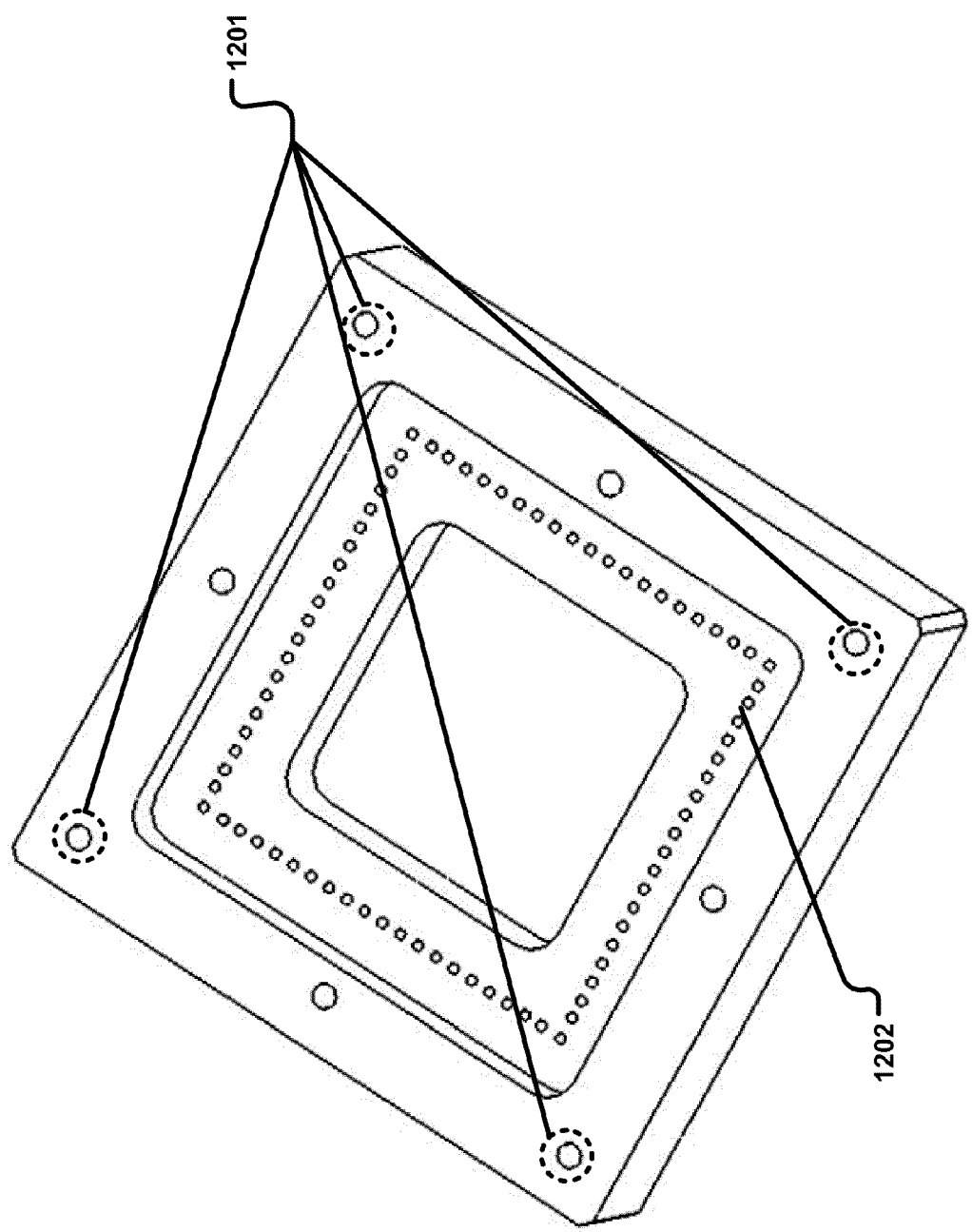
FIG. 12 shows a sketch map of an example welding clamp.

The device used for cell manipulation also includes a welding clamp that ensures the vertical and correct welding of spring-pins. FIG. 12 shows an example of a welding clamp. A welding clamp includes inserting holes 1202 and positioning holes 1201. The position, diameter, and quantity of inserting holes 1202 are matched to the corresponding spring-pins on a PCB of a metal clamp. For example, the inserting holes 1202 ensure that the spring-pins vertically lineup with the PCB 905 on the metal clamp. The positioning holes 1201 are matched to the positioning holes (e.g., positioning holes 1002) on the PCB of the metal clamp.

Figure 13:
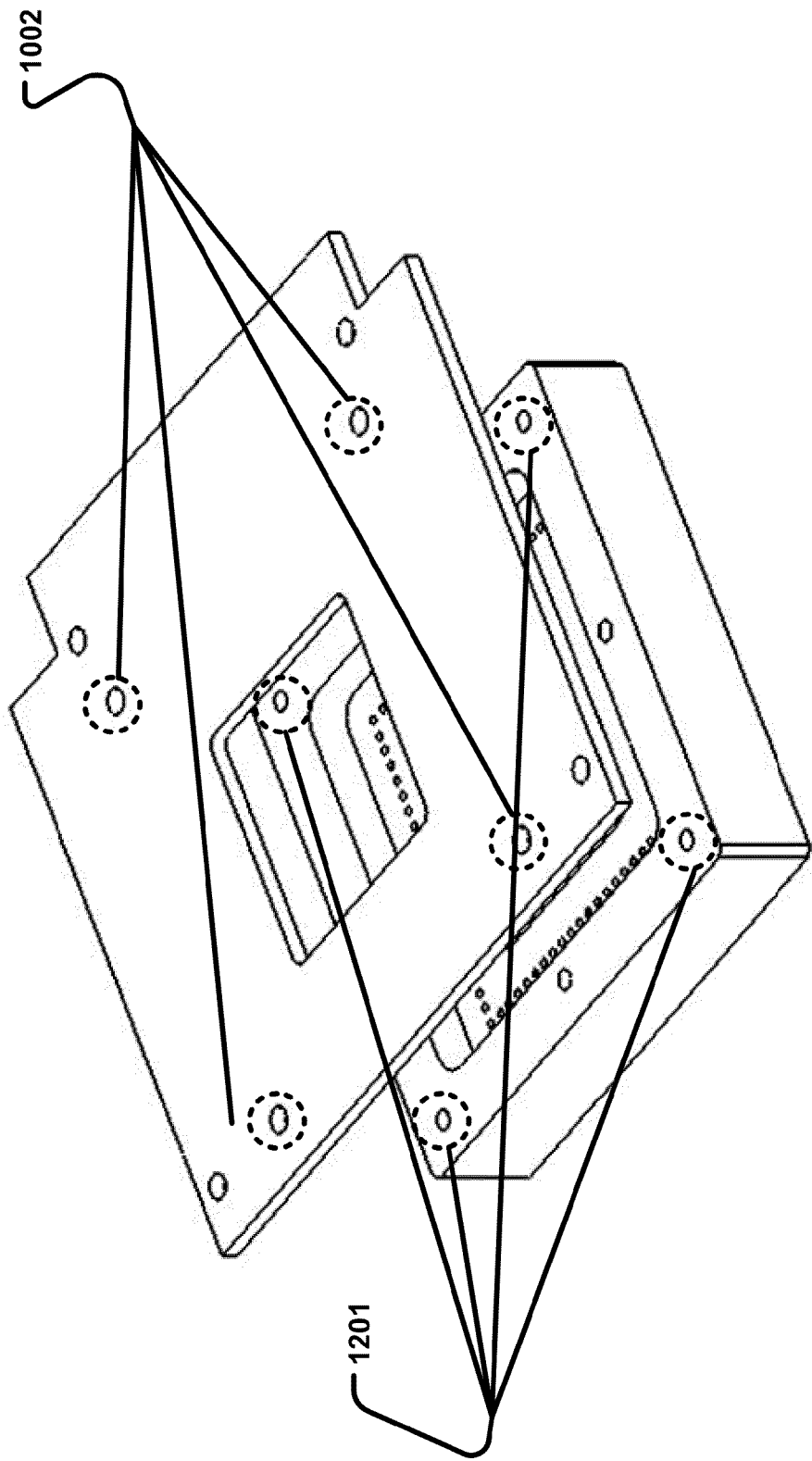
FIG. 13 shows usage of an example welding clamp.

FIG. 13 shows an example usage of a welding clamp. The positioning holes 1201 are used to fix the PCB 905 to the welding clamp through the positioning holes 1002 of the microelectrode sensing device. In addition, the positioning holes 1201 ensure that the spring-pins in the inserting holes 1202 can be inserted into the pads 1005 of the PCB 905 correctly.

Cell Position and Electrophysiological Detection

Figure 14:
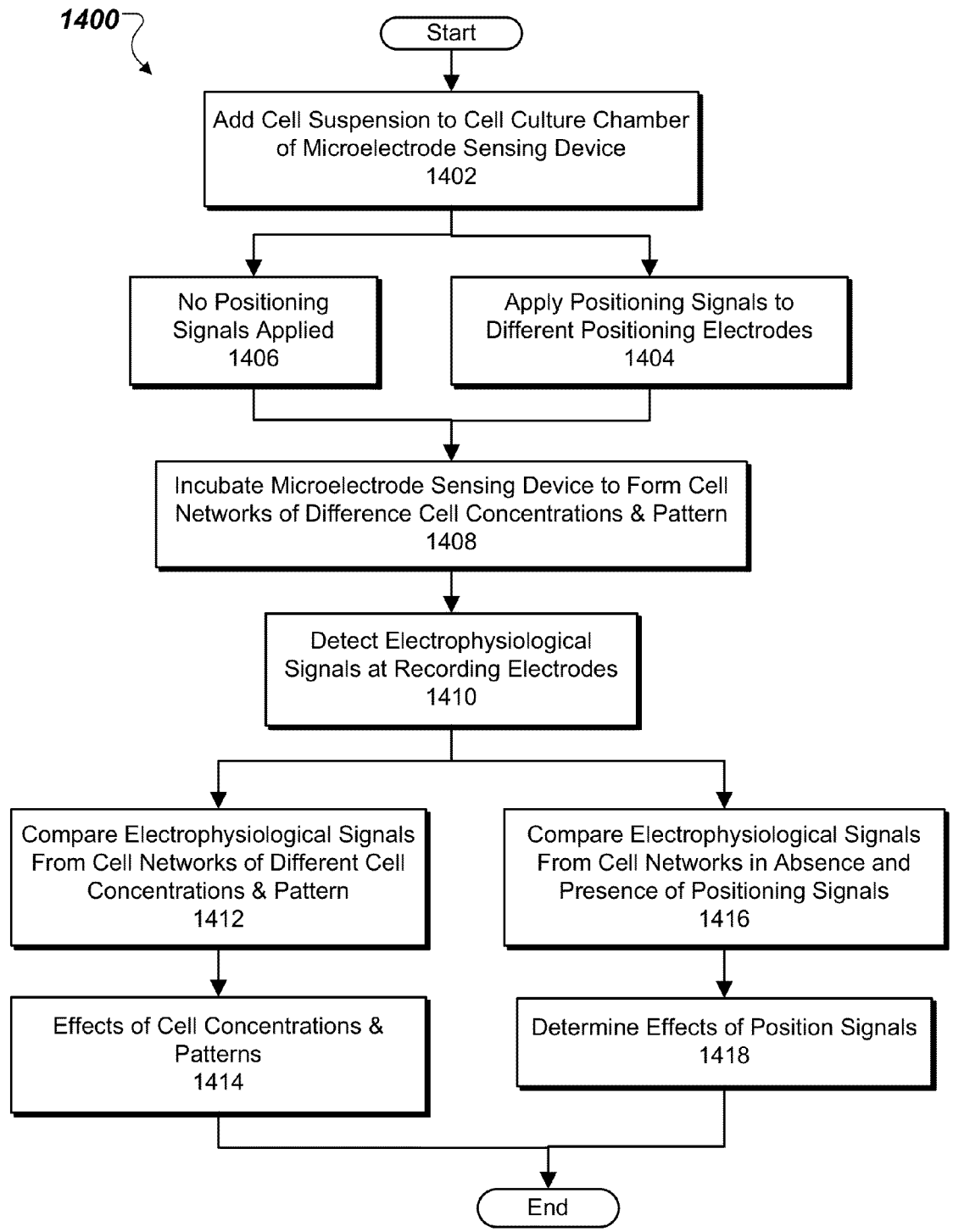
FIG. 14 shows an example process for cell positioning.

FIG. 14 is an experimental flow chart shown an example of cell positioning. A cell suspension, such as neurons is added to a cell culture chamber (e.g., cell culture chamber 106) (1402). Positioning signals are applied to different positioning electrodes to generate a dielectrophoretic force (1404). For example, positioning signals can be applied to all positioning electrodes, or applied to only certain electrodes, in order to construct different cell patterns and/or concentrations. Also, the positioning signals can be applied all the time (i.e., continuously), or applied periodically. For example, one type of the positioning signals can include a pair of 5 MHz, 2 V sinusoidal signals with the phase-angle difference of 180° applied for 30 min. Further, positioning signals are not applied to any of the positioning signals to obtained control measurements (1406).

After the application of the positioning signals, the microelectrode sensing device is incubated to allow the cells to form a cell network (1408). For example, the microelectrode sensing device can be incubated at 37° C. in a humidified incubator containing 5% $CO_2$ atmosphere. For a cell network that includes excitable cells, such as neurons, electrophysiological signals can be detected at different recording electrodes (1410). The electrophysiological signals obtained from cell networks of different cell concentration (due to different applications of different positioning signals to different positioning electrodes) are compared (1412). Based on this comparison, the effect of different cell concentrations and patterns can be obtained (1414). In addition, the electrophysiological signals obtained from the control positioning electrodes (due to no positioning signals applied to any positioning electrodes) are compared against those obtained from different cell concentrations and/or patterns (1416). Based on this comparison, the effects of application of the positioning signals can be determined (1418).

Figure 15:
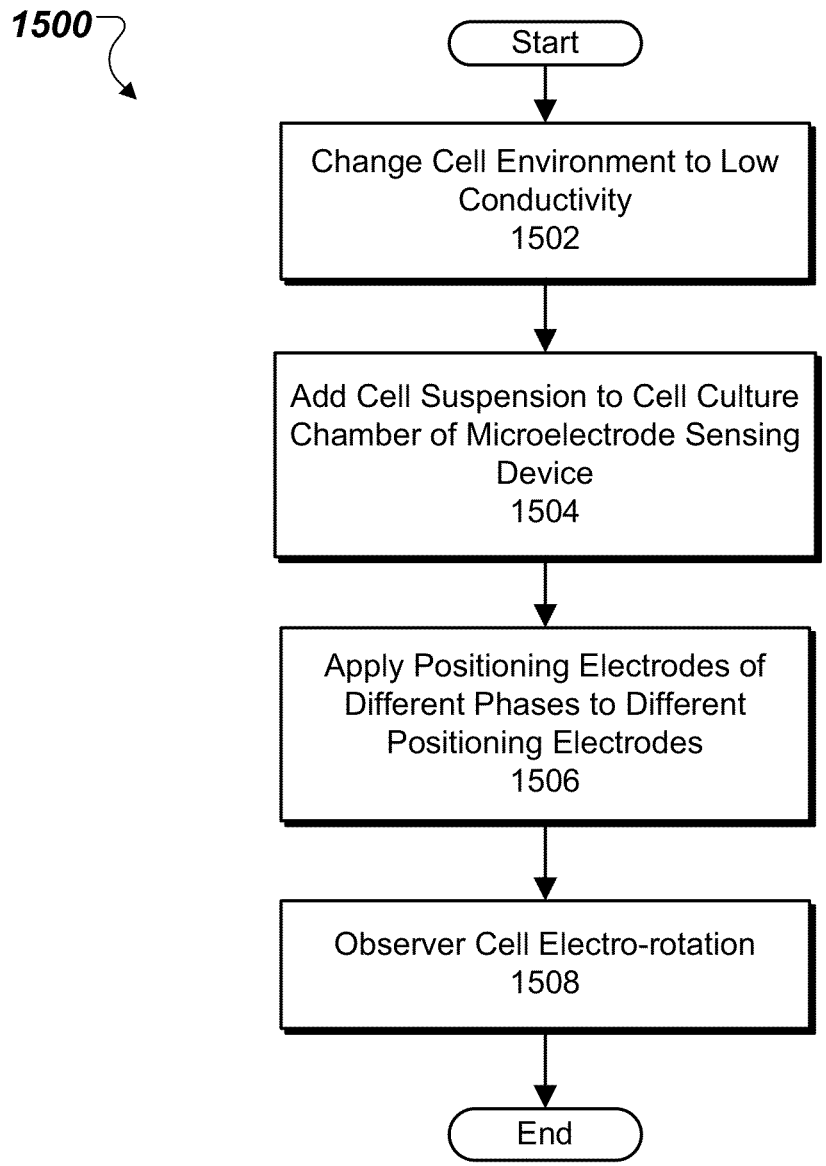
FIG. 15 shows an example process for cell electro-rotation.

FIG. 15 shows an example process for performing cell electro-rotation. The environment of cell suspension is changed to a low conductivity environment (1502). The cell suspension in the low conductivity environment is added to a cell culture chamber of a microelectrode sensing device (1504). Different positioning signals with different phases are applied to different positioning electrodes to form an electric field of rotation (1506). For example, different pairs of sinusoidal signals having different phases can be applied to selective positioning electrodes. Different pairs of positioning signals having the same frequency and amplitude but different phases are applied to selective neighboring electrodes. For example, one or more positioning electrodes are applied with a pair of sinusoidal signals with 0° phase. One or more positioning electrodes are applied with a pair or sinusoidal signals with 90° phase. One or more positioning electrodes are applied with a pair of sinusoidal signals with 180° phase. One or more positioning electrodes are applied with a pair of sinusoidal signals with 270° phase. Cell electro-rotation is observed under a microscope under above conditions (1508).

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications and enhancements to the described examples and implementations and other implementations may be made based on what is disclosed.

What is claimed is:

1. A microelectrode sensing device, comprising:
   a printed circuit board (PCB);
   a chip unit electrically connected to the printed circuit board comprising:
   a substrate,
   a conductive layer positioned over the substrate and comprising one or more recording electrodes,
   a first set of ground electrodes in the conductive layer separated by a first set of gaps and arranged to form a first enclosure around the one or more recording electrodes, wherein a wire connecting each of the recording electrodes to a corresponding contact pad on the chip unit passes through a corresponding gap in the first set of gaps;
   an insulation layer positioned over the conductive layer,
   another conductive layer positioned over the insulation layer comprising at least four positioning electrodes, such that the at least four positioning electrodes and the one or more recording electrodes are in two different conductive layers, wherein the at least four positioning electrodes are configured as a first two-dimensional (2D) electrode array to position cells near the one or more recording electrodes, which are configured as a second 2D electrode array, and wherein each of the recording electrodes in the second 2D electrode array is positioned between four positioning electrodes in the first 2D electrode array;
   a second set of ground electrodes in the other conductive layer separated by a second set of gaps and arranged to form a second enclosure around the at least four positioning electrodes, wherein a wire connecting each of the positioning electrodes to a corresponding contact pad on the chip unit passes through a corresponding gap in the second set of gaps; and
   another insulation layer positioned over the other conductive layer; and
   a cell culture chamber positioned over the chip unit and sealed to the PCB with the chip unit located between the PCB and the cell culture chamber; and
   wherein, the one or more recording electrodes and the at least four positioning electrodes are electrically independent so as to independently receive a stimulus signal at each recording electrode and positioning electrode and independently detect a sensed signal at each recording electrode.

2. The microelectrode sensing device of claim 1, wherein the chip unit is electrically connected to the PCB by wire bonding.

3. The microelectrode sensing device of claim 1, wherein there are two rows of contact pads arranged to surround the chip unit on the PCB; and
   the contact pad of the chip unit are distributed at each edge of the chip unit.

4. The microelectrode sensing device of claim 3, wherein the chip unit is electrically connected to the PCB using electrical connections between the contact pads of the PCB and the contact pads of the chip unit.

5. The microelectrode sensing device of claim 3, further comprising additional contact pads located at each edge of the PCB, wherein at least one of the two rows of contact pads of the PCB that surround the chip unit is electrically connected to the additional contact pads at each edge of the PCB using conductive wires shaped to form an arc.

6. The microelectrode sensing device of claim 3, wherein the contact pads of the chip unit are equally spaced apart at the edge of the chip unit.

7. The microelectrode sensing device of claim 3, wherein each of the recording and positioning electrodes is separately connected to a separate one of the contact pads on the chip unit.

8. The microelectrode sensing device of claim 7, wherein each of the recording and positioning electrodes is separately connected to a separate one of the contact pads on the chip unit using a conductive wire shaped to form an arc.

9. The microelectrode sensing device of claim 8, wherein a width of the conductive wire is shaped to increase from the recording electrodes to the contact pads on the chip unit.

10. The microelectrode sensing device of claim 8, wherein the two conductive layers comprises a plurality of ground electrodes connected through a passage in the insulation layer that is between the two conductive layers and arranged to separate the wire connecting each of the recording and positioning electrodes to the contact pads on the chip unit.

11. The microelectrode sensing device of claim 1, wherein a surface of each recording electrode comprises electroplated spongy material.

12. The microelectrode sensing device of claim 11, wherein the electroplated spongy material comprises platinum black.

13. The microelectrode sensing device of claim 1, wherein the substrate of the chip unit comprises glass wafer.

14. The microelectrode sensing device of claim 1, wherein each positioning electrode is shaped to form a ring.

15. The microelectrode sensing device of claim 1, wherein each insulation layer comprises two layers of $Si_3N_4$ and $SiO_2$.

* * * * *